United States Patent [19]
Allen

[11] Patent Number: 5,580,794
[45] Date of Patent: Dec. 3, 1996

[54] DISPOSABLE ELECTRONIC ASSAY DEVICE

[75] Inventor: Michael P. Allen, Sunnyvale, Calif.

[73] Assignee: Metrika Laboratories, Inc., Sunnyvale, Calif.

[21] Appl. No.: 455,236

[22] Filed: May 31, 1995

Related U.S. Application Data

[63] Continuation of Ser. No. 111,347, Aug. 24, 1993, abandoned.

[51] Int. Cl.$^6$ .................................................. G01N 21/78
[52] U.S. Cl. ...................... 436/169; 422/58; 422/82.05; 422/82.09
[58] Field of Search ........................... 422/56, 58, 82.05, 422/82.08, 82.09; 364/497, 499; 436/169, 170

[56] References Cited

U.S. PATENT DOCUMENTS

| | | | |
|---|---|---|---|
| 4,627,445 | 12/1986 | Garcia et al. | 128/770 |
| 4,806,312 | 2/1989 | Greenquist | 422/56 |

FOREIGN PATENT DOCUMENTS

| | | | |
|---|---|---|---|
| 2019865 | 1/1991 | Canada . | |

*Primary Examiner*—Jeffrey Snay
*Attorney, Agent, or Firm*—Timothy H. Gens

[57] ABSTRACT

A disposable electronic assay device comprising card-like housing containing a sample receptor for receiving a sample of body fluid containing an analyte to be determined, a sample treatment element for reaction with sample fluid components to yield a physically detectable change which correlates with the amount of analyte in the sample, a detector responsive to the physically detectable change for producing an electrical signal which correlates with the amount of analyte in the sample, a signal processor connected to the detector for converting the electrical signal to a digital test result output, and visually readable output means connected to the signal processor for receiving and presenting the test result output. The signal processor can include an analog to digital conversion element for converting an analog reflectance or transmission output signal to a digital reflectance output, processor for converting the digital reflectance or transmission output to a digital test result output. The sample treatment element can include, for example, in fluid communication, a separator for separating interfering substances from the sample, a sample developer for converting the analyte in the sample to a physically detectable substance in an amount which correlates with the amount of the analyte. The sample development element can comprise bibulous material having a sample reaction zone containing reaction chemistry for reacting specifically with the analyte and producing a product with a physically detectable label, the amount of which correlate with the amount of analyte, and a detection zone positioned for interaction with the detector.

31 Claims, 10 Drawing Sheets

DISPOSABLE ELECTRONIC ASSAY DEVICE

This is a Continuation of application Ser. No. 08/111,347, filed on Aug. 24, 1993, now abandoned.

FIELD OF THE INVENTION

This invention relates to a disposable self-contained, electronic assay device for use in determining the amount of one or more analytes in a body fluid such as blood or urine. In particular, this invention relates to a small disposable, electronic credit-card sized device which, upon application of a body fluid to a sample receptor, automatically performs an analysis and presents the concentration of the analyte and/or another message output in readable form.

BACKGROUND OF THE INVENTION

Qualitative and quantitative self-tests have developed gradually over the last half century. Since the first self-test for glucose, introduced 50 years ago, advances in dry reagent chemistry and the technology associated with device design have lead to self-test kits capable of performing complex quantitative analysis from finger stick whole-blood samples by an untrained person. The evolution of self-tests from the initial glucose test of 1941 to the current state-of-the-art non-instrumented whole-blood quantitative cholesterol test (Allen et al, *Clin. Chem.* 36:1591–1597 (1990)) was directed by a number of factors, including the need for testing by consumers in the privacy of their homes.

The first device, called the CLINITEST® for measurement of glucose, was developed by the Ames division of Miles Laboratories and used a dry formulated effervescent tablet that was added to a solution of diluted urine (Free et al, *Lab. Med.* 15:595–601 (1984), Compton and Treneer U.S. Pat. No. 2,387,244 (1945)). The reaction of glucose in the sample with copper sulfate in the tablet produced a color change as a result of a redox reaction, which was then compared to a color block chart to estimate the amount of glucose in the sample. The positive effect of the CLINITEST® on the treatment of diabetes was very real and established for the first time the contribution of convenience in allowing analytical chemistry to be used by the non-technical person.

The above test was then followed in the 1950s by the development of solid-phase dipstick tests for the measurement of glucose and proteins, among others, in urine (Free et al, *Clin. Chem.* 3:163–168 (1957); Comer, *Anal. Chem.* 28:1748 (1956); Free et al, *Gastroenterology* 24:414–421 (1953)); and later in the 1960s and 1970s their measurement in whole-blood samples (Free et al, *Lab. Med.* 15:595–601 (1984); Free et al, *Clin. Chem.* 30:829–838 (1984); Balazas et al, *Lanset* 1:1232 (1970); Kallner, *Clin. Chem.* 3:1–16A (1983). These tests basically involve reaction of the analyte in a sample with reagents on the dipstick pad, resulting in formation of colored product(s). Nature and intensity of color gives the measure of analyte in the sample. For whole blood samples, the red cells are first separated prior to the reaction of plasma with the reagent on the pad. These tests are read visually and provide at best, semi-quantitative results. Availability of portable instruments in the 1970s and 1980s have allowed these dipstick tests to provide quantitative results (Balazas et al, *Lanset 1:1232* (1970); Free, A. H. *Pure Appl. Chem.* 54:2063–2073 (1982). Because of the cost associated with instruments, these quantitative tests have mostly found use in professional markets. Perhaps the most important single exception is the whole-blood quantitative glucose tests for use in the home market. Diabetic patients must monitor their glucose level more than once a day for effective management of the disease with insulin, justifying the cost of the needed instrument.

The next major advancement in non-instrumented tests came with the application of immunochemical reagents on a solid support. This led to a number of commercially useful diagnostic tests including those for HCG (pregnancy), LH, FSH, CKMB, Staphylococcus, and rubella. Measurement of the hormone HCG to detect pregnancy was among the first of these tests to become commercially successful in the home market. The first home pregnancy test, the E.P.T.™ used a solution phase chemical reaction that formed a brown ring on the surface of the urine solution in the presence of HCG. The 2 hour long protocol associated with this test was sensitive to vibration and timing, causing false results. These disadvantages were eliminated during the next decade of evolution, which saw the development of modern solid-state devices.

In the late 1980s, a completely self-contained pregnancy test was introduced by Unipath Ltd. and marketed by Whitehall Laboratories. This test, called the CLEAR BLUE EASY™, had all the reagents dry formulated along a laminated membrane, used conjugated colored latex microbeads as the signal reagent, and used a capillary migration immunoconcentration format. This test is complete in 3 minutes and is the first one-step assay of its kind.

Two additional test systems that appeared in the late 1980s were the LIPOSCAN™ by Home Diagnostics Inc. and the CHEMCARD™ by Chematics Inc. Both tests measure cholesterol in whole-blood using visual color comparison. Since visual color matching is subjective, these tests do not achieve the quantitative performance necessary for cholesterol testing (Pradella, M., et al *Clin. Chem.* 36:1994–1995 (1990).

For many analytes such as the markers for pregnancy and ovulation, qualitative or semiquantitative tests are appropriate. There are, however, a variety of analytes that require accurate quantitation. These include glucose, cholesterol, HDL cholesterol, triglyceride, a variety of therapeutic drugs such as theophylline, vitamin levels, and other health indicators. Generally their quantitation has been achieved through the use of an instrument. Although suitable for clinical analysis, these methods are generally desirable for point-of-care testing in physicians offices rather than in the home due to the expense of the instrument.

Recently, a number of non-instrumented methods for accurate measurement of analytes have started to emerge. The key to achieving instrument-free quantitation is through the use of migration distance rather than color matching as the visual signal. In migration distance assays, chemical/biochemical reactions occur as the analyte is wicked through a solid support. During wicking the analyte reacts with a signal-producing reagent and forms a visible signal along the support. The migration distance or the distance of signal border is related to analyte concentration. The operator reads the height of the color bar, much the same way one reads a thermometer, and finds the concentration from a calibrated scale.

There are only a handful of migration-type assays commercially available. These include the ENVIRONMENTAL TEST SYSTEMS QUANTAB™, which measures chloride in swimming pools and during the mixing of concrete; Syva's ACCULEVEL® for the measurement of therapeutic drugs; and ChemTrak's ACCUMETER® for measurement of cholesterol in whole-blood. Other companies such as Enzymatics and Crystal Diagnostics have more recently announced the introduction of their Q.E.D.™ and CLIN-IMETER™ technologies to measure alcohol in saliva and cholesterol in blood. ActiMed Laboratories describes the newest thermometer-type assay device (Ertinghausen, G., U.S. Pat. No. 5,087,556 1992).

These single use thermometer-type non-instrumented devices (for quantitation) and the non-instrumented color comparison devices for qualitative measurement represent the state-of-the-art at this time. Although these devices have shown adequate performance, they have several problems associated with reliability and convenience. First and foremost, the colors generated on these devices are not always uniform and sharp. In the case of the migration type assays the border is often light in color, unclear and difficult to read. This translates directly to user errors since the user must make a judgment related to the position of the color band border. In the case of the non-instrumented pregnancy tests it is sometimes difficult to visually interpret the intensity of the colored spot (especially at HCG concentrations close to the cut-off sensitivity) and result interpretation is sometimes a problem. Any time a non-technical operator is required to make a visual judgment or interpretation, an error is possible and sometimes unavoidable. Second, the assay protocol for these tests is sometimes difficult and lengthy taking 15 minutes to 1 hour to obtain a result. Third, these tests often do not have sufficient procedural and reagent controls to assure adequate test performance. Fourth, non-instrumented devices can only measure endpoint type tests (enzyme rate cannot be measured), and therefore, the potential analyte menu is limited.

A recent article in Clinical Chemistry (Daviaud, et al, *Clin. Chem.* 39:53–59 (1993)) evaluated all 27 home use pregnancy tests sold in France. The authors state, "among the 478 positive urine samples distributed, 230 were falsely interpreted as negative. The main explanation for such a high percentage of false negative results was difficulty in understanding the explanatory leaflets accompanying the kits and hence in reading the results". Clearly there is room for improvement in what is currently state-of-the-art.

The device of this invention is a disposable, single use electronic instrument that is entirely self-contained, including all chemistry reagents. The user simply adds a body fluid sample, and minutes later a numerical digital result appears on the display. The device provides procedure and reagent check systems that permit the device to achieve a high level of reliability. The numerical display overcomes the most significant problem associated with non-instrumented devices. The subject invention marks a significant step in the evolution of self-tests.

Small instruments, some pocket-sized, which measure glucose or other analytes are commercially available and common in use. Examples of these instruments are glucose meters manufactured by Boeringer Mannheim, Miles, Lifescan, Medisense, Home Diagnostics, and Kyoto Daiichi. However, these meters are intended for continued daily use over months and years, and they are too complex and expensive to be discarded after a single use.

OBJECTS AND SUMMARY OF THE INVENTION

It is an object of this invention to provide an entirely self-contained, disposable instrument combining miniaturized electronics and chemistry reagents capable of qualitative and/or quantitative measurement of single or multiple analytes of clinical interest by non-technical users. The device is fully self-contained with all electronic and chemistry reagents necessary for sample analysis contained within the device. The device is about the size of a credit card (2 in.×3 in.), and the entire device including the electronics and chemistry reagents will be sufficiently inexpensive to allow the device to be discarded or recycled after a single use. This invention is the state-of-the-art in single use disposable devices and represents a significant advancement in user friendly self-tests.

In summary, the device of this invention is a disposable electronic assay device comprising card-like housing containing a sample receptor means for receiving a sample of body fluid containing an analyte to be determined, a sample treatment means for reaction with sample fluid components to yield a physically detectable change which correlates with the amount of analyte in the sample, a detector means responsive to the physically detectable change for producing an electrical signal which correlates with the amount of analyte in the sample, signal processing means connected to the detector means for converting the electrical signal to a digital test result output, and visually readable output means connected to the signal processor means for receiving and presenting the test result output.

In one preferred device, the physically detectable change is a change in reflectivity or transmission of an output surface, and the detector comprises a light source positioned to direct light on the output surface and a light detector positioned to receive light reflected or transmitted by the output surface to yield a reflectance output signal.

The signal processing means can include an analog to digital conversion means or current integrating comparitor means for converting an analog reflectance output signal to a digital reflectance output or an analog transmission output signal to a digital transmission output, processor means for converting the digital reflectance or transmission output to a digital test result output.

These sample treatment means can include, for example, in fluid communication, a separation means for separating interfering substances from the sample, a sample development means for converting the analyte in the sample to a physically detectable substance in an amount which correlates with the amount of the analyte. The separation means can include a filtration means. In one preferred device, the sample development means comprises bibulous material having a sample reaction zone containing reaction means for reacting specifically with the analyte and producing a product with a physically detectable label, the amount of which correlates with the amount of analyte, and a detection zone positioned for interaction with the detector means. The physically detectable label can provide a change in reflectance in the detection zone which correlates to the amount or concentration of the label on the detection zone. The physically detectable label can be, for example, a chromophore, fluorophore, chemuluminesore, colloidal elemental metal or metal compound.

DETAILED DESCRIPTION OF THE PREFERRED EMBODIMENTS

Figure 1:
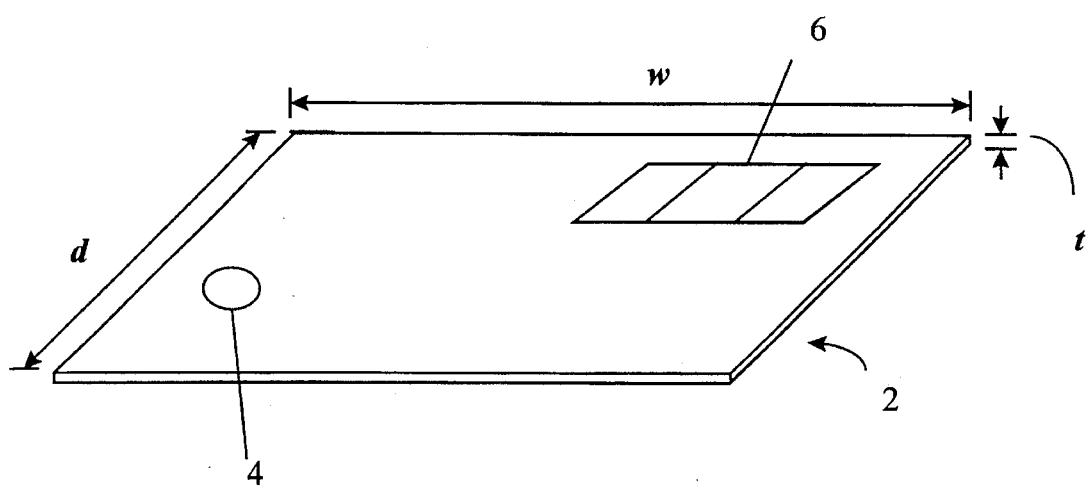
FIG. 1 is an isometric view of the embodiment of the disposable device of this invention.

It is an object of this invention to provide an instrument which preferably has the following features:
1) Low cost of less than about $5.00 manufacturing cost.
2) Stability of 6 months to 24 months.
3) Self-contained power source (battery or solar cell).
4) Capacity to measure one or several analytes at one time.
5) Auto-start in response to sample application or removal of the assay from the foil pouch into the light which activates the solar cell.
6) Auto instrument and reagent zero in response to sample application or removal of the device from the foil pouch into the light which activates the solar cell.
7) Auto read in response to sample presence in a location down stream from the optical system or after a time interval following sample application or after a time interval after the device is removed from the foil pouch and placed in the light which activates the solar cell.
8) Auto start for the "reference" and "read" functions that uses circuit closure between two contacts that are immersed in the sample or auto start as a result of the device being placed in the light.
9) Converts reflectance or transmission into clinical units after the reading is stabilized based on a pre-programmed algorithm.
10) Measure reflectance or transmission at several time points until stabilized.
11) Can measure reaction endpoint or reaction rate.
12) Integrated light source (LED).
13) Integrated light detector(s).
14) Numeric display that retains the value for at least 10 minutes and has at least 3 digits.
15) A display that can show a message such as POS or NEG, GO SEE YOUR DOCTOR, or the like.
16) Custom integrated processor containing analog to digital converter, LCD driver, quad amp, multiplex switch and latches with unitized light source, detector, battery, LCD, and all sensing electrodes for low cost.
17) Ambient light suppression.
18) Temperature compensation.

The chemistry is self-contained within the instrument and dry formulated on a solid matrix (i.e. membrane) where reflectance is used or lyophilized and deposited in a reaction compartment or spotted and dried in a reaction compartment where transmission is used or present on an electrode where the chemistry produces a change in electrical current or pH. The chemistry operates in response to the analyte to produce a color change within the chemistry matrix or in a fluid defined by the sample (i.e. plasma) and reconstituted reagents or the chemistry will produce a change in electrical current (i.e. produce or consume electrons) or cause a pH change that can easily be detected. This type of chemistry is common in home glucose instruments than contain chemistry reagents impregnated in a reagent strip.

Substantially all types of common clinical assays can be carried out on this system. Assays that can be done include, but are not limited to, general chemistry assays for analytes such as glucose, cholesterol, HDL cholesterol, LDL cholesterol, triglycerides, and BUN; and immunoassays for therapeutic drugs like theophylline, digoxin, and phenobarbital, drugs of abuse such as THC, morphine, cocaine, amphetamine, methamphetamine, PCP, and LSD; and antibodies such as HIV antibody, and proteins like C-reactive protein and enzymes like alkaline phosphatase, CKMB or Pro Thrombin.

Single or multiple assays can be done at one time. For example, a single assay can be done measuring cholesterol or one device can be set up to measure both total and HDL cholesterol form a single sample. One test device can be set up to measure one, two, three, or more analytes at one time.

Qualitative and quantitative assays can be done. For example, a pregnancy test or a drugs of abuse assay need not be quantitative and the display may read POS or NEG. Other tests like theophylline, and digoxin, or cholesterol and HDL cholesterol require quantitative results. In this system it is possible to display both a quantitative and qualitative result. For example, if a cholesterol value is 280 mg/dl, the display may read 280 mg/dl HIGH RISK—SEE YOUR DOCTOR.

This device of this invention is ideal for on site testing in remote locations throughout the world in health fairs, occupational health settings, physician offices, and in the home. The device can include automatic reagent handling (sample filtration, component separation, blood separation or the like), automatic sample measurement, automatic reagent delivery, and on board controls such that non-technical users can operate the test easily without prior training. Also since the device uses a digital display (like a calculator) there is no need for visual interpretation of color quality or intensity or visual reading of a signal migration distance. Thus, user errors will be significantly reduced using this disposable electronic device. The device can be used for qualitative and quantitative measurement of many analytes of clinical interest including, but not limited, to cholesterol, HDL and cholesterol, triglyceride, glucose, qualitative HCG (pregnancy), quantitative HCG (ectopic pregnancy), C-reactive protein (CRP), tumor markers, HIV antibodies, enzymes, drugs of abuse, and therapeutic drugs using both general chemistry and immunoassay methods. Both endpoint and reaction rate type assays can be accomplished using this device.

One of the key features of this invention is the inexpensive cost of the device such that it becomes economically practical for the device to be used as a single use, disposable unit.

The device includes an electronic component, a chemistry reagent component, and a housing which contains the electronics and chemistry. It is desirable that the electronics and housing are integrated into a single piece. However, the reagent strip can be replaced once or several times such that the electronics is re-used.

Referring to the drawings, FIG. 1 is an isometric view of the an embodiment of the disposable device of this invention. The device 2 has a sample receptor 4 and a visual readout display 6 such as a liquid crystal display. The thickness "t", width "w" and depth "d" can be varied to provide the desired overall dimensions. The device can be of any convenient size and may likely be the size of a credit card with dimensions of about 8 cm long by 5 cm wide and 0.2 cm deep. The optimal dimensions of the device will be determined by several factors including: 1) the size of electronic components, 2) the size of the chemistry components, and 3) marketing consumer studies. The device preferably is 7 cm long, 2.5 cm wide and 0.5 cm thick. The device may assume any convenient shape including square, rectangular, triangular, oval, round or any other desired geometric shape as long as the electronics and chemistry can be cost effectively contained with acceptable performance.

The instrument is designed for a single use and can measure either transmission, reflectance, electrical current or pH change, for example. The instrument is fabricated in a unitized integrated format to reduce cost of manufacture. The instrument may have the following generally described components: light source such as a light emitting diode (LED); optics which may be as simple as a clear coating over the light source and/or detector; a detector which senses reflected or transmitted light; a processor with memory which controls the assay start and stop, receives and processes input from the detector, stores assay calibration information and the like; an analog to digital convertor or the like (a current integrating comparator can be used); a power source which can be a battery or solar cell or any convenient power source; a temperature compensation mechanism (optional); and a liquid crystal display (LCD) with 1 to 6 digits (most likely 3 digits). The instrument described may contain one, all, or none of the above-mentioned components or may contain other components that are necessary for the diagnostic reflectance or transmission instrument to operate.

Figure 2:
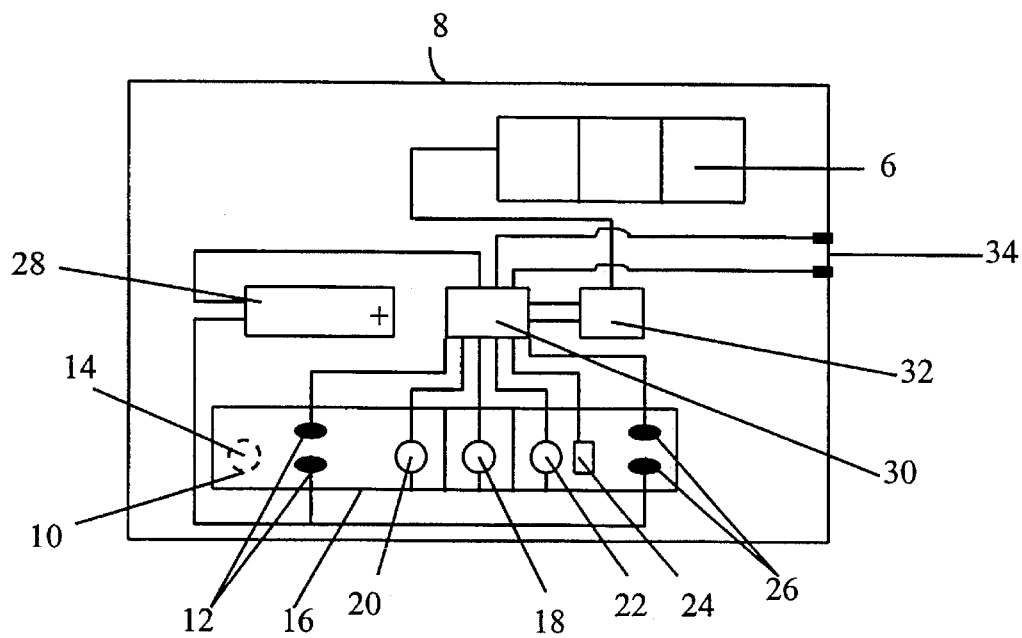
FIG. 2 is a schematic view of the device of this invention, showing one configuration of the electronic and sample processing components for single analyte testing.

FIG. 2 is a schematic view of the device of this invention designed for reflectance measurements of the detectable signal, showing one configuration of the electronic and sample processing components for single analyte testing. Mounted in housing 8 are all of the components, including power supply required to conduct the assay. The reagent strip 10 has electrode pair 12 mounted thereon between the sample application zone 14 and the reagent zone 16 to detect the presence and movement of sample liquid on the reagent strip. Presence of sample liquid bridging the electrode pair reduces the resistance across the electrodes, signaling the presence of a conductor (sample liquid) therebetween. LED 18 is positioned between the detectors 20 and 22. The detectors 20 and 22 are conventional light detectors, selected to detect light reflected at a preselected wavelength corresponding to a property of the physically detectable label. Temperature sensor 24 is mounted on the reagent strip to detect the temperature of the system and provide ambient temperature information for calibration adjustment at temperature extremes. The electrode pair 26 is positioned to detect movement of sample liquid beyond the detection zone occupied by the light sensors.

The power source 28 has a lead from its negative pole connected to one side of the electrode pairs 12 and 26, and a lead from its positive pole being connected to the power connector of the analog to digital converter 30. The analog to digital converter has an output lead leading to LED 18, input leads leading to light detectors 20 and 22, leads leading to temperature sensor 24. The processor and memory component 32 is connected to the analog to digital converter 30 and LCD 6. External calibration ports 34 are connected to the analog to digital converter 30.

This embodiment of FIG. 2 includes two sets of electrodes (12 and 26) which function is to turn the instrument on in one of two modes when the sample is present by using the conducting properties of the sample to complete the circuit between the electrodes. Electrode set 12 is the "reference-on" electrode which is positioned immediately down stream from the sample application port. The sample comes into contact with this electrode set almost immediately after application onto the device. The instrument calibrating-to-self-zero feature is energized allowing the light source to warm up and the optical system (LED, detector, and optics) to zero by taking readings on the unreacted reagent area. Electrode set 26 is called the "read-on" electrode which is positioned at the end of the chemistry reagent area down stream from electrode set 12 and down stream from the optical system. When the sample reaches this electrode set the chemistry reactions are well underway and the instrument begins to read the reagent system. The reading may begin immediately when the sample reaches electrode set 26 or there may be some time delay of about less than 1 second to 10 minutes (preferably from about 30 seconds to 2 minutes). There may be single or multiple readings or the readings may continue until the reagent system response has stabilized either to an endpoint or to a constant reaction rate.

The instrument functions of automatic zero and read are initiated in response to the presence of a sample. The electrode method is described above, however, any convenient and inexpensive method can be used. Another method uses a solar cell which activates when the device is removed from the light-impermeable foil storage pouch. When the user removes the device from the pouch the ambient light turns the instrument on and activates the self-reference and allows the LED and optics to warm up. This also initiates a timer on the processor which automatically activates the "read on" function after a specified time. This system eliminates the need for the "reference on" and "read on" electrode pairs.

The optical system may include the components listed below. However, this system is not limited to only these components and may use any state-of-the-art, common or custom electronics, whatever is necessary. The optical system may include a light source such as an LED, a detector and an optical surface. The optical surface may or may not be necessary and may be as simple as a clear or transparent coating over the light source and detector. A simple aperture can be used in lieu of a lens to focus and meter the light. The coating can be any plastic or silicone or glass or the like. The optical systems of the device may be set up to measure single or multiple analytes. For single analytes only one light source and detector is necessary; for two analytes, two sets of light source and detector is necessary and so on. It is possible and preferable to use only one light source and light piping (or lenses) to direct light from one source to several targets. This is a cost saving measure.

The processor 32 can be any common or custom integrated circuit with memory. The processor must have the capacity to either store a set of pre-programmed calibration curves or have the capability to be programmed during device manufacturing. In the case of preprogrammed calibration, a method of curve selection during manufacture is necessary. This can be done by laser burning of a selection of circuit pathways or any convenient means. In the case of post manufacture calibration, a method to load calibration data onto the chip is necessary, for example external calibration contacts 34. External calibration can be accomplished with external electrical contacts or may be done in a non-contact method using radio waves, magnetic fields, pulse light, laser or the like. The non-contact method of calibration may be more practical and efficient from a manufacturing viewpoint.

The processor 32 will also control the entire operation of the instrument including, but not limited to, turning the instrument "reference-on" and "read-on" in response electrode power or time signals; timing, recording, and processing the instrument zero function; controlling any time delays or timed steps during reading; determining when the reaction has stabilized; receiving and processing information from the temperature sensor; and receiving input from the optical system and converting it to output based on calibration information to the display. The processor will also calculate the time taken for the sample to travel from electrode set 12 to electrode set 26 and if too much time is taken an error code will show on the display. Also the processor will determine if the chemistry reaction has occurred within the specified time or to a specified endpoint range or reaction rate range to control for inactive reagents. Any other electronic control checks can also be included.

The power source 28 can be any convenient device including, but not limited to, a battery or a solar cell. The shelf life of the final product will be 6 months to 24 months at room temperature. The power source must have stability consistent with this product dating. Use of a solar cell would have the advantage of allowing the instrument to initiate and auto zero immediately after he assay device is taken out of the storage foil pouch. This would eliminate the need for electrode set 12 ("reference-on" electrodes).

The display 6 will be a liquid crystal display (LCD) or any convenient inexpensive device. The number size in the display must be sufficient large to allow that substantially all persons can read the assay value. Older people may have poor vision and they must be considered. The display height may be from 0.5 cm to 2.0 cm most likely about 0.75 cm to 1.25 cm. The number of digits in the display can be anywhere from 1 to about 10 digits, however, most assays require only 3 digits and therefore the display in this device will likely have a 3 to 5 digit display. In addition to showing the assay result, the display may show error messages such as "SAMPLE VOLUME OK" and "RESULT OK".

In the case of a device measuring one analyte, only one display is necessary. In the case where two or more analytes are measured simultaneously, then at least two display configuration options exist which include a single display which alternates between results with only one result on the display at one time, or two or more results being shown on the display at one time. For example, if both total cholesterol and HDL cholesterol are measured then the display can alternate between the total and HDL values or show both values at one time. The ideal situation would be having all values displayed simultaneously. However, manufacturing cost is a consideration.

In the case of a qualitative assay, the display may read POS or NEG; YES or NO; HIGH or LOW; or the like. The display can also say something like "GO SEE YOUR DOCTOR" or "YOUR TEST IS POSITIVE, HOWEVER CONFORMATION BY YOUR DOCTOR IS RECOMMENDED" or any convenient message. This type of message display will be helpful in instructing or counseling non-technical users especially for assays detecting a life-threatening condition, such as AIDS. The display can also be used to interpret a quantitative value. For example, if a cholesterol value is displayed as 280 mg/dl, the display may also say "HIGH RISK—GO SEE YOUR DOCTOR".

Figure 3:
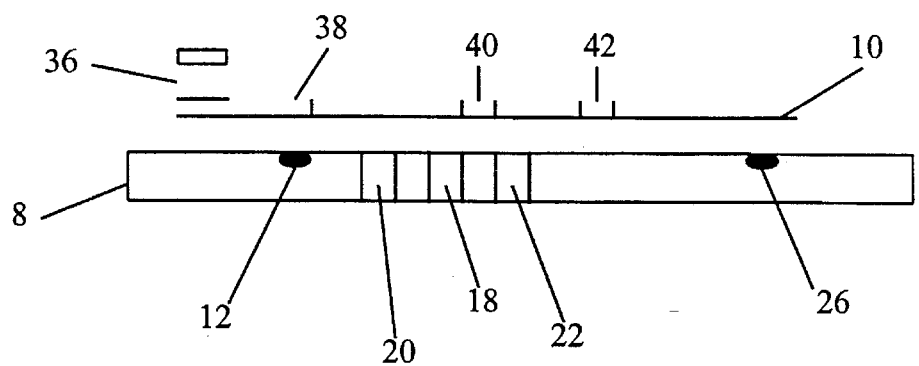
FIG. 3 is an exploded cross-sectional side view of one configuration of the sample processing components for single analyte testing.

FIG. 3 is an exploded cross-sectional side view of one configuration of the sample processing components for single analyte testing. The reagent strip 10 rests on a lower plate of housing 8 supporting the electrodes 12 and 26, LED 18 and detectors 20 and 22. The solids separation device 36 rests on the input end of strip 10. The strip includes a plurality of zones 38, 40 and 42, the functions of which will be described in detail hereinafter.

The chemical reagents are dry formulated on a matrix which can be any convenient bibulous material including, but not limited to, paper such as WHATMAN 1C, 2C, 31 ET or S&S 903C, 470, 604 or the like; synthetic membranes such as Millipore IMMOBILON, Pall nylon, S&S nitrocellulose, cellulose acetate, regenerated cellulose, Gelman VERSAPORE or the like. The assay matrix 10 an be any convenient bibulous material including porous plastics such as polyethylene and polypropylene such as products made by Porex Technologies Corp. or synthetic or natural mesh screens such as those made by Tetko. The sample filtration and blood separation components 36 can be constructed using synthetic membranes, fibrous depth filters such as glass fiber, plastic fiber, metal fiber, cellulose fiber or the like or any combination or filters and membranes.

The housing 8 for the device can be made of any convenient material including, but not limited to, thermoplastics such as polyethylene, DELRIN, ABS and polystyrene.

Figure 4:
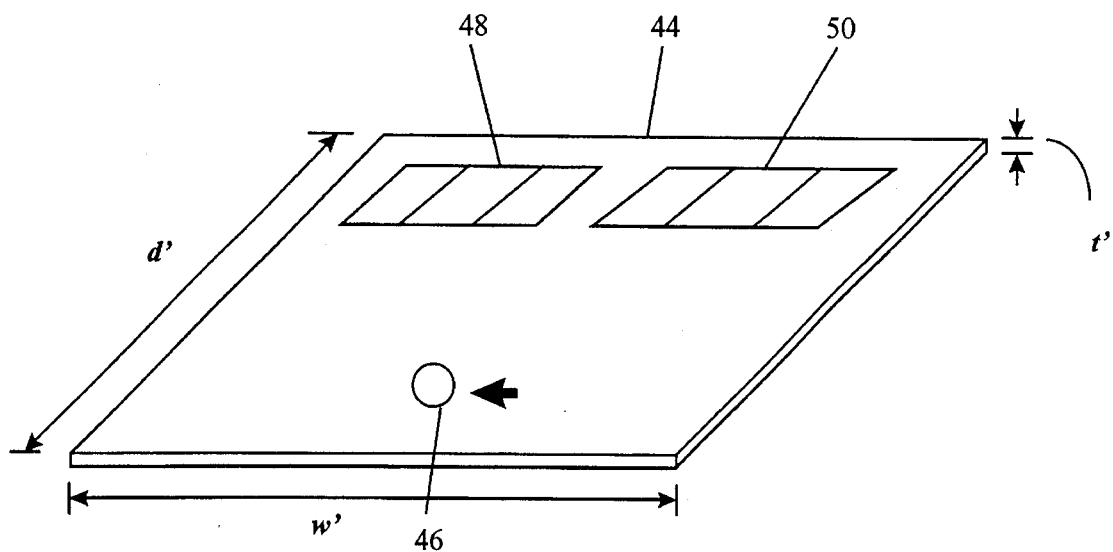
FIG. 4 is an isometric view of the embodiment of the disposable device of this invention for two analyte testing.
Figure 5:
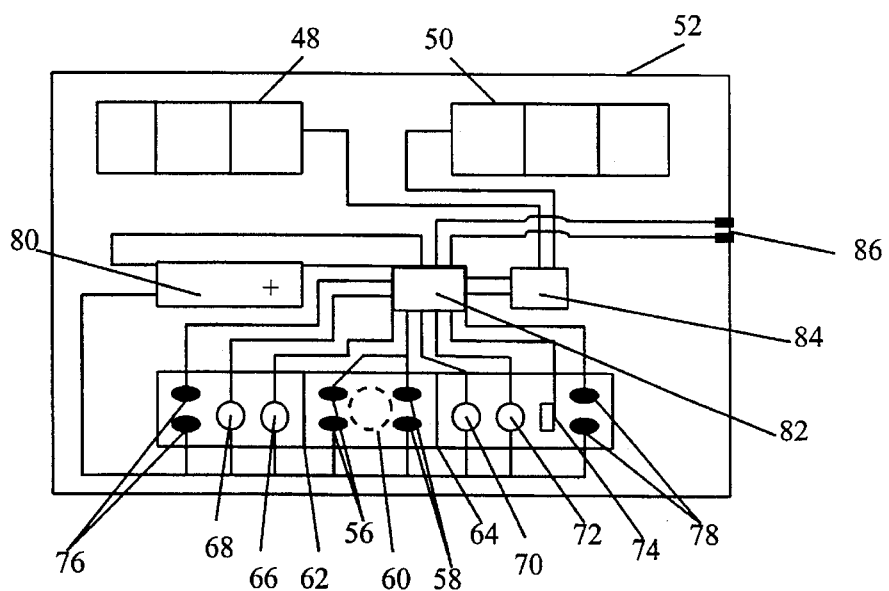
FIG. 5 is a schematic view of the device of FIG. 4, showing one configuration of the electronic and sample processing components for two analyte testing.
Figure 6:
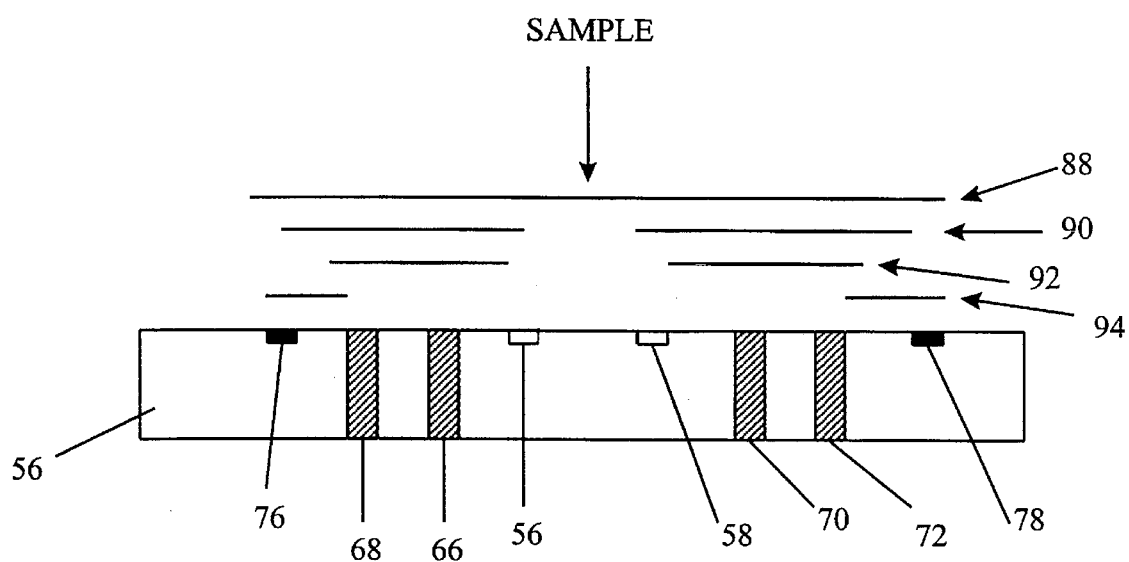
FIG. 6 is an exploded cross-sectional side view of one configuration of the sample processing components for two analyte testing in the embodiment of FIGS. 4 and 5.

FIG. 2 shows an embodiment with one optical system which measures one analyte and FIGS. 4–6 show an embodiment with two optical systems allowing measurement of two analytes simultaneously. Three, four, five, or more analytes may be measured simultaneously in the same manner.

FIG. 4 is an isometric view of the embodiment of the disposable device of this invention for two analyte testing. FIG. 5 is a schematic view of the device of FIG. 4, showing one configuration of the electronic and sample processing components for two analyte testing. FIG. 6 is an exploded cross-sectional side view of one configuration of the sample processing components for two analyte testing in the embodiment of FIGS. 4 and 5. The device 44 has a sample receptor 46 and visual readout displays 48 and 50 such as liquid crystal displays. The thickness "t'", width "w'" and depth "d'" can be varied to provide the desired overall dimensions and can have the same relative dimensions of the embodiment shown in FIGS. 1–3.

Referring to FIG. 5, mounted in housing 52 are all of the components, and power supply required to conduct the assay. The reagent strip 54 has electrode pairs 56 and 58 mounted thereon between the sample application zone 60 and the reagent zones 62 and 64 to detect the presence and movement of sample liquid on the reagent strip. As in the embodiment of FIG. 2, presence of sample liquid bridging each electrode pair reduces the resistance across the respective electrodes, signaling the presence of a conductor (sample liquid) therebetween. LED 66 is positioned adjacent detector 68, and LED 70 is positioned adjacent detector 72. The detectors 68 and 72 are conventional light detectors, selected to detect light reflected at a preselected wavelength corresponding to a property of the physically detectable label. Temperature sensor 74 is mounted on the reagent strip to detect the temperature of the system, and provide ambient temperature information for calibration adjustment at temperature extremes. The electrode pair 76 is positioned to detect movement of sample liquid beyond the detection zone occupied by the light sensor 68, and electrode pair 78 is positioned to detect movement of sample liquid beyond the detection zone occupied by the light sensor 72.

The power source 80 has a lead from its negative pole connected to one side of the electrode pairs 76, 56, 58 and 78 and a lead from its positive pole being connected to the power connector of the analog to digital converter 82. The analog to digital converter has output leads leading to LEDs 66 and 70, input leads leading to light detectors 68 and 72, and leads leading to temperature sensor 74. The processor and memory component 84 is connected to the analog to digital converter 82 and LCDs 48 and 50. External calibration ports 86 are connected to the analog to digital converter 82.

This embodiment of FIG. 4 includes four sets of electrodes (76, 56, 58 and 78) whose function is to turn the instrument on in one of two modes when the sample is present by using the conducting properties of the sample to complete the circuit between the electrodes. Electrode sets 56 and 58 are the "reference-on" electrode which are positioned immediately down stream from the sample application port. The sample comes into contact with these electrode sets almost immediately after application onto the device. The instrument self-zero feature is energized allowing the light source to warm up and the optical system (LED, detector, and optics) to zero by taking readings on the unreacted reagent area. Electrode sets 76 and 78 are called the "read-on" electrodes, positioned at the end of the chemistry reagent areas down stream from electrode sets 56 and 58 and down stream from the optical systems. When the sample reaches electrode sets 76 and 78, the chemistry reactions are well underway and the instrument begins to read the reagent system. The reading may begin immediately when the sample reaches electrode sets 76 and 78, or there may be some time delay of about less than 1 second to 10 minutes (most likely of about 30 seconds to 2 minutes). There may be single or multiple readings or the readings may continue until the reagent system response has stabilized either to an endpoint or to a constant reaction rate.

The instrument functions of automatic zero and read are done in response to the presence of a sample. The electrode method is described above, however, any convenient and inexpensive method can be used. Another method uses a solar cell which is activated when the device is removed from the light-impermeable foil storage pouch. When the user removes the device from the pouch the ambient light turns the instrument on and activates this self-reference and allows the LED and optics to warm up. This also initiates a timer on the processor which automatically activates the "read on" function after a specified time. This system eliminates the need for the "reference on" and "read on" electrode pairs.

As described above with respect to FIG. 3, the optical system may include the components listed below. However, this system is not limited to only these components and may use any state-of-the-art, common or custom electronics, whatever is necessary. The optical system may include a light source such as an LED, a detector and an optical surface. The optical surface may or may not be necessary and may be as simple as a clear or transparent coating over the light source and detector. A simple aperture can be used in lieu of a lens to focus and meter the light. The coating can be any plastic or silicone or glass or the like. The optical systems of the device may be set up to measure single or multiple analytes. For single analytes only one light source and detector is necessary; for two analytes, two sets of light source and detector is necessary and so on. It is possible and preferable to use only one light source with light piping (or lenses) to direct light from one source to several targets. This is a cost saving measure.

The processor 84 can be any common or custom integrated circuit with memory. The processor must have the capacity to either store a set of pre-programmed calibration curves or have the capability to be programmed during device manufacturing. In the case of pre-programmed calibration, a method of curve selection during manufacture is necessary. This can be done by laser burning of a selection of circuit pathways or any convenient means. In the case of post manufacture calibration, a method to load calibration data onto the chip is necessary, for example external calibration contacts 86. External calibration can be accomplished with external electrical contacts or may be done in a non-contact method using radio waves, magnetic fields, pulse light, laser or the like. The non-contact method of calibration may be more practical and efficient from a manufacturing viewpoint.

The processor 84 will also control the entire operation of the instrument including, but not limited to, turning the instrument "reference-on" and "read-on" in response electrode signals power or time; timing, recording, and processing the instrument zero function; controlling any time delays or timed steps during reading; determining when the reaction has stabilized; receiving and processing information from the temperature sensor; and receiving input from the optical system and converting it to output based on calibration information to the display. The processor will also calculate the time taken for the sample to travel from electrode sets 56 and 58 to electrode set 76 and 78, and if too much time is taken, an error code will show on the display. Also the processor will determine if the chemistry reaction has occurred within the specified time or to a specified endpoint range or reaction rate range to control for inactive reagents. Any other electronic control checks can also be included.

The power source 80 can be any convenient device including, but not limited to, a battery or a solar cell. The shelf life of the final product will be 6 months to 24 months at room temperature. The power source must have stability consistent with this product dating. Use of a solar cell would have the advantage of allowing the instrument to initiate and auto zero immediately after he assay device is taken out of the storage foil pouch. This would eliminate the need for electrode sets 56 and 58 ("reference-on" electrodes).

The displays 48 and 50 will be a liquid crystal display (LCD) or any convenient inexpensive device. The number size in the display must be sufficient large to allow that substantially all persons can read the assay value. Older people may have poor vision and they must be considered. The display height may be from 0.5 cm to 2.0 cm most likely about 0.75 cm to 1.25 cm. The number of digits in the display can be anywhere from 1 to about 10 digits, however, most assays require only 3 digits and therefore the display in this device will likely have a 3 to 5 digit display. In addition to showing the assay result, the display may show error messages such as "SAMPLE VOLUME OK" and "RESULT OK". For example, if both total cholesterol and HDL cholesterol are measured, then the display can alternate between the total and HDL values or show both values at one time. The ideal situation would be having all values displayed simultaneously. However, manufacturing cost is a consideration.

In the case of a qualitative assay, as described above with respect to the embodiment shown in FIGS. 1–3, the displays may read POS or NEG; YES or NO; HIGH or LOW; or the like. The displays can also say something like "GO SEE YOUR DOCTOR" or "YOUR TEST IS POSITIVE, HOWEVER CONFORMATION BY YOUR DOCTOR IS RECOMMENDED" or any convenient message. This type of message display will be helpful in instructing or counseling non-technical users especially for assays detecting a life-threatening condition, such as AIDS. The display can also be used to interpret a quantitative value. For example, if a cholesterol value is displayed as 280 mg/dl, the display may also say "HIGH RISK—GO SEE YOUR DOCTOR".

FIG. 6 is an exploded cross-sectional side view of one configuration of the sample processing components for two analyte testing of the embodiment shown in FIGS. 4 and 5. The reagent strips rests on a lower plate of housing 54 supporting the electrodes 76, 56, 58 and 78 and detectors 68 and 72. The sample transport matrix 88, separation membrane 90, reaction membrane 92 and adhesive layer 94 secures together layers 88, 90 and 92.

The housing, matrix, membrane materials and chemical reagents are as described above with respect to FIG. 3.

Figure 7:
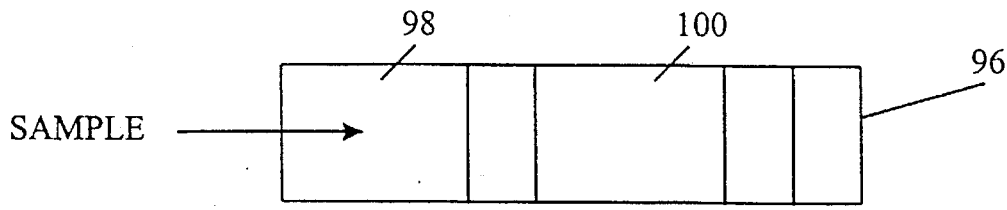
FIG. 7 shows a top view of a dry reagent configuration that can be used for general chemistry assays.
Figure 8:
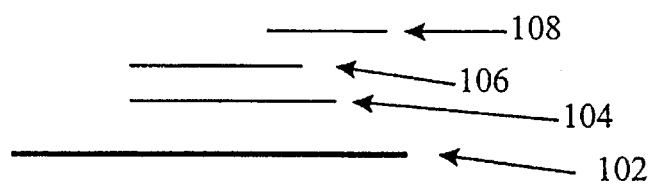
FIG. 8 is an exploded view of a lengthwise cross section of the reagent strip shown in FIG. 7.

FIGS. 7 and 8 shows a dry reagent configuration that can be used for general chemistry assays including, but not limited to, glucose, cholesterol, HDL cholesterol, LDL cholesterol, and triglyceride. A similar dry reagent configuration is disclosed in Canadian patent applications 2,020,029 and 2,019,865 and U.S. Pat. No. 5,132,716, the entire contents of which are hereby incorporated by reference. FIG. 7 is a top surface view and FIG. 8 is an exploded view of a lengthwise cross section of the reagent strip. The strip design includes assay chemistry and a blood separation device. Methods for constructing the assay chemistry devices of the embodiments shown in FIGS. 7 and 8 are described in Canadian Application No. 2,020,029 filed Jun. 26, 1990; Canadian Application No. 2,019,865 filed Jun. 26, 1990; Canadian Application No. 2,028,965 filed Oct. 31, 1990; European Application No. 90307137.1 (Pub. No. 0430395 A1, Jun. 29, 1990); U.S. Pat. No. 5,135,716 and U.S. Ser. No. 07/379,009, the entire of contents of each of the listed patents and patent applications being hereby incorporated by reference.

Referring to FIG. 7, the surface of the strip 96 comprises a sample application zone 98 and a reaction zone 100. The strip can have a width of about 7 mm and each of the zones can have a length of about 10 mm.

The four layers shown in FIG. 8 include the sample transport matrix 102, separation membrane 104, the reaction membrane 106, and adhesive layer 108. The layers are in fluid communication. The sample transport layer 102 is designed to accept the sample and move it horizontally across the entire assay length underneath the separation and reaction membranes. This sample movement takes about 10 seconds to 5 minutes (most usually 15 seconds to 3 minutes). After horizontal movement of the sample in the transport matrix, the sample moves upward and red-cells are substantially removed by the separation membrane 104. The red cell free plasma is collected in the reaction membrane 106 where the analyte in the sample reconstitutes and reacts with the reagents immobilized in this area. A color change is produced such that the color intensity on the reaction membrane is proportional to the concentration of analyte. The instrument reads the color intensity by reflection and converts the reading to clinical units which is shown on the display.

The sample transport matrix 102 extends the entire length of the assay strip and is composed of any bibulous material including, but not limited to, fabric or mesh made of cotton, nylon, polyester, polypropylene, polyethylene or the like; paper such as WHATMAN 31ET or 3 MM; glass fiber such as WHATMAN GFA, GFD, S&S 3362 or 32; plastic fiber, or metal fiber or any hydrophilic synthetic membrane. The sample transport area can be untreated or have various reagents diffusively or non-diffusively immobilized, such as stabilizing proteins, detergents, anticoagulants like heparin or EDTA, LDL precipitating reagents, antibodies, or red cell agglutinating agents like wheat germ lectin or anti-human RBC. The length of the sample transport is about 10 mm to 50 mm most usually about 26 mm in length and 3 to 15 mm in width (most usually 5 mm to 10 mm in width).

The separation membrane 104 and the reaction membrane 106 are micro-porous synthetic membranes of pore size from $0.2\mu$ to $12\mu$ (most usually $0.4\mu$ to $7\mu$). The separation membrane and the reaction membrane can be used 5 mm to 20 mm in length (most usually about 9 mm to 15 mm in length) and 3 mm to 15 mm in width (most usually about 5 mm to 10 mm in width). Examples include: Pall nylon, S&S nitrocellulose, cellulose acetate, regenerated cellulose, Gelman ULTRABIND, Millipore IMMOBILON or the like.

The separation membrane may be untreated or can be coated with proteins, dextrans, sugars, or carbohydrates for red cell stabilization, LDL precipitating reagents such as magnesium chloride and dextran sulfate, antibodies, or red cell agglutinating agents to facilitate red cell removal.

The reaction membrane has all signal producing reagents diffusively or non-diffusively immobilized. In the case of a cholesterol assay the reaction membrane would be dipped in a solution including the following and then dried:

1) 18 U/ml cholesterol esterase (EC:3.1.1.13)
2) 50 U/ml cholesterol oxidase (ED:1.1.3.6)
3) 5 µg/ml horseradish peroxidase
4) 1 wt. % Triton X-100
5) 1 wt. % Sodium Cholate
6) 200 µg/ml 3,3', 5,5' tetramethylbenzidine dihydrochloride (TMBD)
7) 0.1M phosphate pH 7

The adhesive layer 108, used to secure the layers together, can be any type of adhesive including, but not limited to, epoxy, hot melt glue or any commercially available glue or tape.

Figure 9:
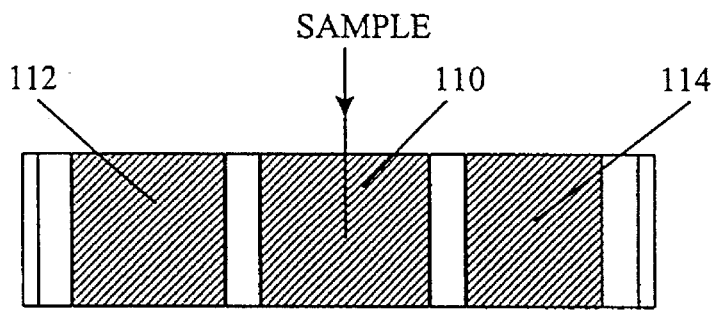
FIG. 9 shows a top view of a dry reagent configuration that can be used for general chemistry assays for two analytes.
Figure 10:
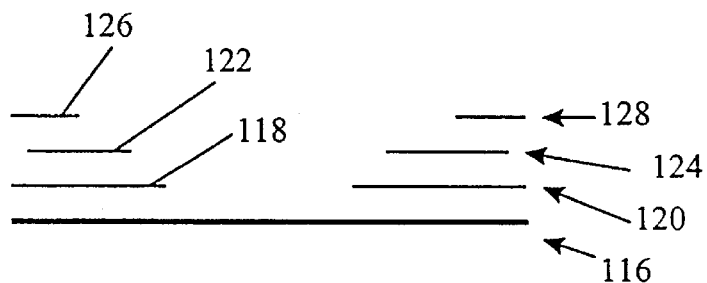
FIG. 10 is an exploded view of a lengthwise cross section of the reagent strip shown in FIG. 9.

FIGS. 9 and 10 show an assay strip that measures two general chemistry analytes at one time from one sample. The duel assay strip uses the same strip configuration described above for FIGS. 7 and 8, with the exception that the transport area is now 42 mm long and the sample is applied between the two reaction surfaces. The multiple assay example shown in the FIGS. 9 and 10 can be for HDL and total cholesterol, and LDL lipoproteins will have to be removed prior to measurement in the case of the HDL assay.

This can be accomplished by diffusively immobilizing 2 μM dextran sulfate and 100 mM Mg chloride to the HDL side of the transport matrix.

FIG. 9 shows a top view of a dry reagent configuration that can be used for general chemistry assays for two analytes, and FIG. 10 is an exploded view of a lengthwise cross section of the reagent strip shown in FIG. 9.

FIG. 9 shows a top view of a dry reagent configuration that can be used for general chemistry assays for two analytes, and FIG. 10 is an exploded view of a lengthwise cross section of the reagent strip shown in FIG. 9. Referring to FIG. 9, the two test strip has a sample application zone 110, HDL reaction zone 112 and cholesterol reaction zone 114. Referring to FIG. 10, the strip is constructed with a series of layers, the sample transport matrix 116, separation membranes 118 and 120, reaction membranes 122 and 124 and adhesive layers 126 and 128.

FIGS. 11–21 show various embodiments of immunoassay strip configurations that can be used in the disposable instrument here described. The immunoassay configurations presented here can measure small molecules (haptens) or large molecules (usually proteins). The immunoassays can be set up to be either qualitative in the case of HCG (pregnancy), drugs of abuse, and infectious diseases or quantitative in the case of theophylline, digoxin, quantitative HCG (ectopic pregnancy), C-reactive protein, and CKMB.

Since the subject device is designed for use on-site and in the home, the device must have sample filtration and separation. Whole-blood from a finger stick will be used and since the assay chemistry can operate only on serum or plasma, the red cells must be substantially removed by the device prior to chemical analysis.

Each of the immunoassay configurations shown in FIGS. 13–21 have a sample filtration/blood separation device included. In addition, the immunoassay configurations presented have a common general structure.

Figure 11:
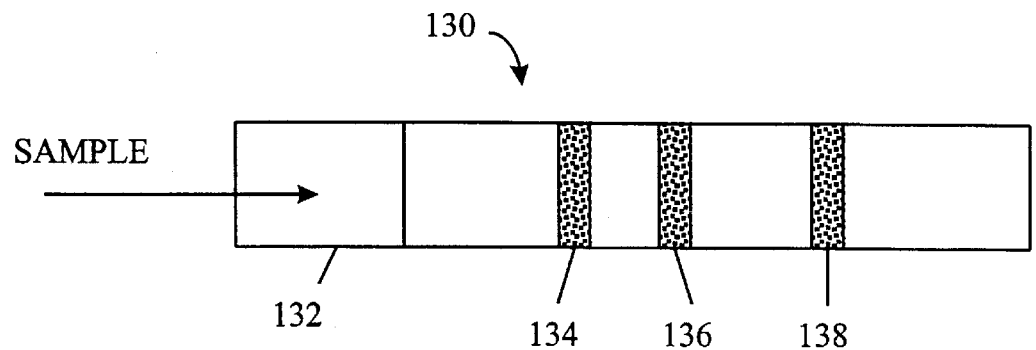
FIG. 11 shows a top surface view of an embodiment having a typical structure with a sample filtration/blood separation device.
Figure 12:
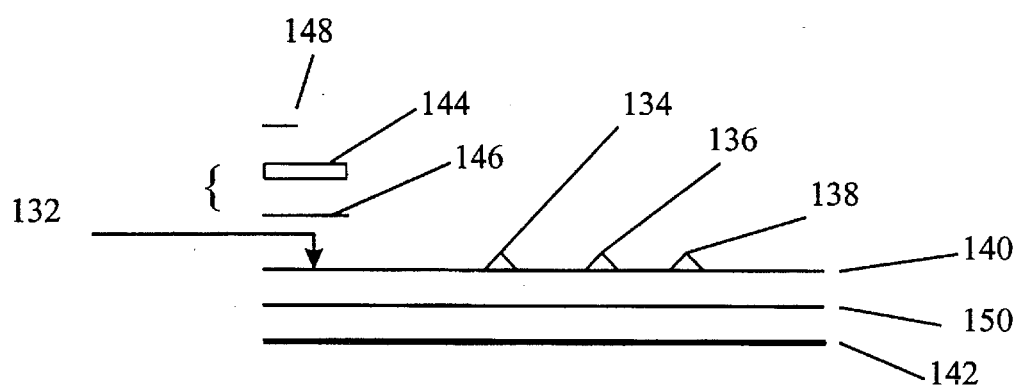
FIG. 12 shows an exploded lengthwise cross section of the embodiment of FIG. 11.

FIG. 11 shows a top surface view of an embodiment having a typical structure with a sample filtration/blood separation device, and FIG. 12 shows an exploded lengthwise cross section of the embodiment of FIG. 11. The overall length of the strip can be anywhere from 3 cm to 20 cm (most likely 4 cm to 10 cm) and the width can be 0.2 cm to 1.5 cm (most likely 0.3 cm to 0.7 cm). The strip shown in FIG. 11 is preferably 5 cm long and 0.5 cm wide. Although the assay strip can contain any number of zones, there are four zones shown in FIG. 11 along the length of the assay strip each containing assay reagents diffusively or non-diffusively bound. The assay strip can contain two, three, four, five or more zones (whatever is necessary to carry out the chemistry). The strip can be one continuous section or be composed of one, two, three or more sections. Each zone may be a separate bibulous material all in fluid communication or one or more zones can be a common material with the other zones being separate materials.

Zone 132 on the strip 130 is located at or slightly downstream from the site of sample application and zone 134 can be directly adjacent or separated by a bibulous spacer in fluid communication downstream from zone 132. Zone 136 can be directly adjacent to zone 134 or be separated in fluid communication downstream from zones 132 and 134, and zone 138 can be directly adjacent to zone 136 or separated in fluid communication downstream from zones 132, 134 and 136. All zones are in fluid communication with each other and with the sample application area. The sample application area can be the same area as zone 132 or the sample application area can be a separate area directly adjacent and upstream from zone 132. Zones 132, 134, 136, and 138 can be 0.05 cm to 1.5 cm in length (most usually 0.1 cm to 1.0 cm in length).

The assay strip including each of the four zones can be composed of the same or different bibulous materials. Examples of materials which can be used include but are not limited to: cellulose papers such as WHATMAN 1C, 2C, 4C, 31ET, S&S 903C, GB002; membranes such as S&S nitrocellulose, cellulose acetate, regenerated cellulose at pore sizes from 1μ to 20μ, Pall nylon at pore sizes of 1μ to 20μ, Gelman ULTRABIND, Millipore IMMOBILON; composite papers or membranes made from mixtures of glass fiber, plastic or metal fiber, cellulose, cellulose acetate, nitrocellulose, regenerated cellulose; or synthetic or natural mesh or fabric made from cotton, cellulose, polyethylene, polyester or nylon.

Zones 132, 134, 136 and 138 can contain reagents diffusively or non-diffusively bound including, but not limited to, antibodies, antigens, enzymes, substrates, small molecules, proteins, recombinant proteins, viral or bacterial lysate, receptors, sugars, carbohydrates, polymers like PVA, and detergents.

The plastic backing 142 in FIG. 12 may or may not be necessary to provide structural support and if necessary can be of any convenient material that provides support for the assay matrix including cellulose acetate, polyester, vinyl or the like at thicknesses of 0.002 inch to 0.015 inch (most usually 0.005 inch to 0.010 inch thick), or synthetic or natural fabric or mesh. The adhesive 150 can be any double stick adhesive including 3M 415, 443, 9460 or the like.

The sample filtration/blood separation device is composed of one, two, or several layers of depth filter 144 such as glass fiber, metal fiber, synthetic fiber, paper, or natural or synthetic fabric and a membrane 146 such as S&S cellulose acetate, nitrocellulose, regenerated cellulose at pore sizes from 0.2μ to 7μ, nucleopore or poretics polycarbonate at pore sizes of 0.2μ to 5μ. The blood separation device is designed to remove substantially all of the red cells from the blood sample, leaving plasma to operate in the assay. As shown in FIG. 12, the sample filtration is positioned immediately above and in fluid communication with strip zone 132. The fiber and membrane can be 0.5 cm to 1 cm in length and are secured with adhesive as shown or are held in the place by the instrument housing. The adhesive layers 148 and 150 can be any convenient adhesive including epoxy, hot melt glue, or the like or adhesive tape like that made by 3M company.

FIGS. 13–21 will now be considered. Each is an immunoassay format that can have a sample filtration/blood separation device as described above in FIGS. 11 and 12 and will have either 3 or 4 reagent zones and a sample application area.

Figure 13:
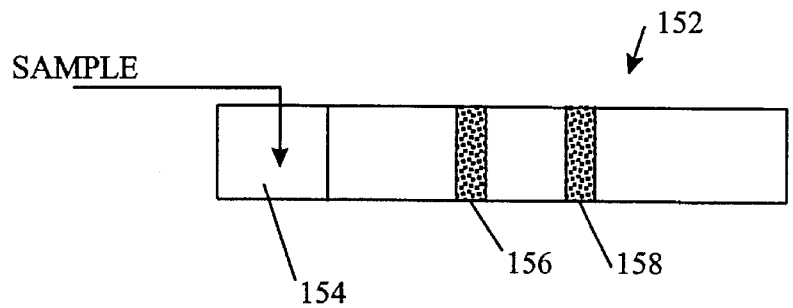
FIG. 13 shows a top surface view of one embodiment of the HIV assay strip.
Figure 14:
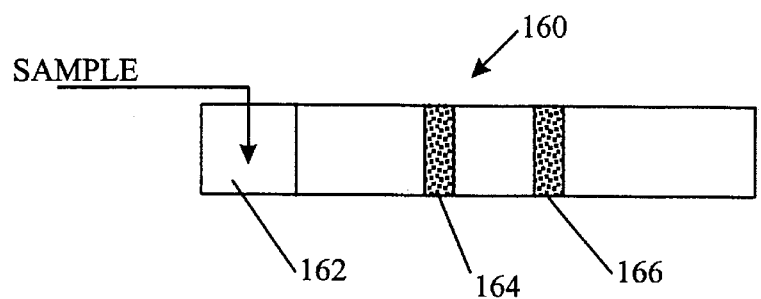
FIG. 14 shows a top surface view of a second embodiment of the HIV assay strip.
Figure 15:
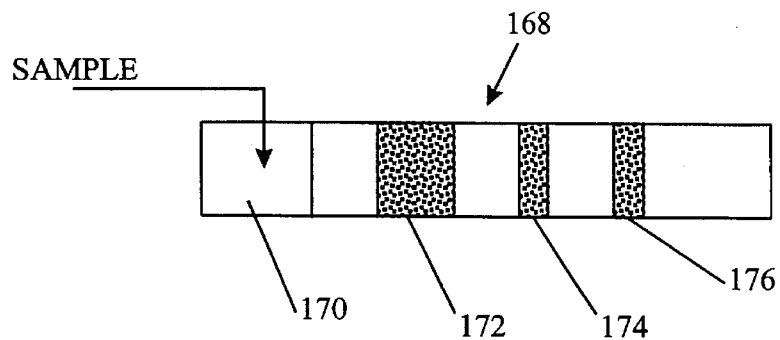
FIG. 15 shows a top surface view of a third embodiment the assay strip.

FIGS. 13–15 shows three embodiments of a qualitative assay to detect HIV antibody in human blood, serum, plasma, saliva, and urine. FIG. 13 shows a top surface view of one embodiment of the HIV assay strip. In the assay strip 152, zone 154 contains diffusively bound conjugate of colloidal gold (or colored latex bead or enzyme such as HRP or alkaline phosphatase) to anti-human antibody and bovine serum albumin (BSA). The BSA serves only as an antigen label that will not cross react with human proteins. Alternately, this antigenic label can be any non-human protein or small molecule such as fluorescein or dinitrophenyl or the like. Ideally, an antigenic label will be chosen for which high affinity ($K_a > 10^7$) antibodies against the label are commercially available. Zone 156 contains non-diffusively bound HIV antigen such as p24 viral protein or viral lysate. Zone 158 contains non-diffusively bound anti-BSA.

In the assay operation, the sample is applied through the sample filtration device to zone 154 where the sample first comes in contact with the conjugate. The anti-human antibody on the conjugate binds to all the human antibody present in the sample, including the anti-HIV antibody. The serum sample and conjugate move along the strip by wicking action and flow through zone 156, where the non-diffusively bound HIV antigen causes the binding of HIV antibody present in the sample. Since the HIV antibody has colloidal gold or enzyme label as a result of the binding to the anti-human antibody in zone 154, a color will concentrate in zone 156 in response to the present of anti-HIV in the sample. If no anti-HIV is present in the sample, signal is not seen in zone 156 since the conjugate cannot bind to this area and flows past. The anti-BSA in zone 158 will always bind the conjugate and will serve as a positive control such that the instrument will make a comparison of the color intensity in zone 156 and zone 158, and based on a calibration, provide a positive or negative result on the display.

FIG. 14 shows a top surface view of a second embodiment of the HIV assay strip. In this embodiment, zone 162 of the assay strip 160 contains diffusively bound conjugate of colloidal gold or enzyme and HIV p24 antigen and BSA. Zone 164 contains non-diffusively bound anti-p24. Zone 166 contains anti-BSA non-diffusively bound.

In this embodiment, the sample is applied through the sample filtration device to zone 162 where the anti-HIV in the sample binds to the p24 antigen of the conjugate. The sample and conjugate then move via capillary and wicking action and flow through zone 164 where the p24 on the conjugate can bind to the immobilized antl-p24 only in the case of a negative sample, since in a positive sample the p24 antigen is already bound by sample anti-HIV. Therefore, in a negative sample (a sample without anti-HIV) the conjugate would bind to the anti-p24 in zone 164 and cause a signal to concentrate. In a positive sample the conjugate p24 antigen is already bound and cannot bind to zone 164, and no (or relatively little) signal is deposited. Thus, a positive sample has little color and a negative sample has color. This type of assay has been called an inverse read assay since the presence of signal indicates a negative result. The anti-BSA in zone 166 will always bind the conjugate and will serve as a positive control such that the instrument will make a comparison of the color intensity in zone 164 and 166, and based on a calibration, provide a positive or negative result on the display.

FIG. 15 shows a top surface view of a third embodiment the assay strip. Zone 170 of strip 168 contains a conjugate of colloidal gold (or enzyme) to p24 antigen, BSA, and a conjugate of colloidal gold (or enzyme) to fluorescein. Zone 172 contains anti-human antibody non-diffusively bound in high concentration. Zone 174 contains anti-BSA non-diffusively bound. Zone 176 contains anti-fluorescein non-diffusively bound.

In this embodiment, the sample is applied through the sample filtration device to zone 170 where the anti-HIV in the sample binds to the p24 on the conjugate forming an anti-HIV-p24-gold-BSA complex. The sample and conjugates move via wicking action through zone 172 where the anti-HIV of the complex formed in zone 170 can bind to the anti-human antibody non-diffusively bound in this zone. Thus, in the presence of anti-HIV in the sample the conjugate is removed from the sample and when the sample reaches zone 174, no signal will form. In the case of a negative sample (without anti-HIV), the complex does not form in zone 170, and the p24-gold-BSA conjugate will migrate to zone 174 and become bound, resulting in a signal. This is an inverse read type assay as previously described. The anti-fluorescein in zone 176 will always bind the gold-fluorescein conjugate and will serve as a positive control such that the instrument will make a comparison of the color intensity in zone 174 and 176, and based on a calibration, provide a positive or negative result is on the display.

Figure 16:
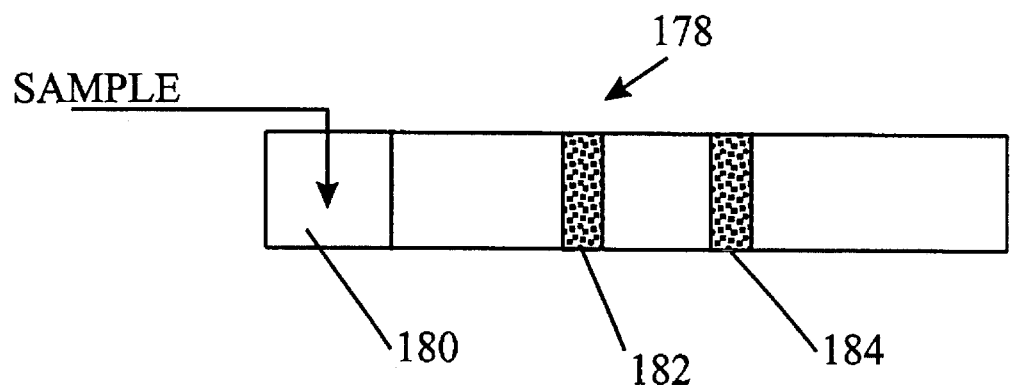
FIG. 16 shows a top surface view of an embodiment of a qualitative and quantitative assay for HCG in urine or serum or whole-blood.

FIG. 16 shows a top surface view of an embodiment of a qualitative and quantitative assay for HCG in urine or serum or whole-blood. Zone 180 of strip 178 contains a conjugate of polyclonal anticz-αHCG to colloidal gold. Zone 182 contains mouse anti-βHCG non-diffusively bound. Zone 184 contains anti-polyclonal HCG non-diffusively bound.

In this embodiment, the sample is applied through the sample filtration device to zone 180 where the α subunit of HCG in the sample binds to the polyclonal anti-HCG of the conjugate. The sample and conjugate move via wicking action and flows through zone 182 where the β subunit of HCG will bind to the antibody immobilized in this area, forming an antibody sandwich of HCG and thereby immobilizing the gold. This is a positive read assay where signal is concentrated in zone 182 in response to the presence of HCG in the sample. The more HCG in the sample will result in more color intensity in zone 182. The anti-polyclonal HCG in zone 184 will always bind the conjugate regardless of the presence or concentration of the HCG in the sample. This zone will serve as a positive high level control such that the instrument will make a comparison of the color intensity in zone 182 and 184, and based on a calibration, provide a positive or negative result or a numerical concentration in clinical units on the display.

FIGS. 17-21 show several different embodiments for an immunoassay that can quantitatively and qualitatively measure proteins or haptens in whole-blood (using the blood separation device), serum, plasma, saliva, or urine.

Theophylline is used as an example analyte, however, substantially all proteins and small molecules can be measured using these assay methods. Although colloidal gold are used in the examples, enzymes or colored latex beads can be used as the signal producing label.

Figure 17:
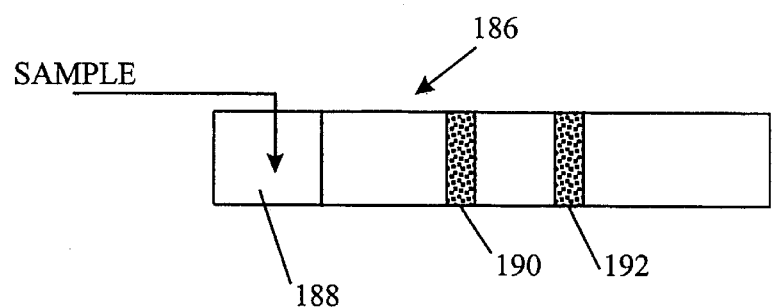
FIG. 17 shows a top surface view of an embodiment for an immunoassay measuring theophylline.

FIG. 17 shows a top surface view of an embodiment for an immunoassay measuring theophylline. In this embodiment, zone 188 of strip 186 contains diffusively bound conjugate of colloidal gold (or enzyme), theophylline and BSA. Zone 190 contains anti-theophylline non-diffusively immobilized. Zone 192 contains anti-BSA non-diffusively bound.

In this embodiment, the sample is applied through the sample filtration device to zone 188 where the sample theophylline and the conjugate mixture moves via capillary migration and wicking through zone 190, where the sample theophylline and the conjugated theophylline compete for the anti-theophylline biding sites in this area. In the presence of very high concentrations of sample theophylline (free theophylline), the binding sites will be substantially all occupied by free theophylline and little or no conjugated theophylline will bind in this area. Thus, this is an inverse read assay and high concentrations of theophylline give low amounts of signal in zone 190. Samples without theophylline will give a maximum of color intensity on zone 190, and intermediate concentrations of theophylline will produce a different color intensity in zone 190 that is inversely proportional to the theophylline concentration. The anti-BSA in zone 192 will always bind the conjugate and will serve as a positive control such that the instrument will make a comparison of the color intensity in zone 190 and 192, and based on a calibration, provide a positive or negative result or a numerical concentration on the display.

Figure 18:
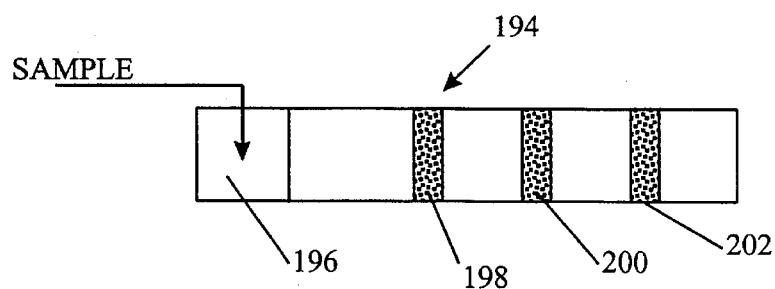
FIG. 18 is a top surface view of a second embodiment of a theophylline immunoassay.

FIG. 18 is a top surface view of a second embodiment of a theophylline immunoassay. In this embodiment, zone 196 of strip 194 has a mouse anti-theophylline diffusively immobilized. Zone 198 contains a conjugate of a colloidal gold or enzyme to theophylline and BSA. Zone 200 contains anti-mouse antibody non-diffusively immobilized. Zone 202 contains anti-BSA non-diffusively immobilized.

In this embodiment, the sample is applied through the sample filtration device to zone 196 where the theophylline sample binds to the mouse anti-theophylline. The sample and the anti-theophylline-theophylline complex moves via capillary and wicking action through zone 198 where the conjugate can bind to excess anti-theophylline such that the higher the concentration of theophylline in the sample, the less mouse anti-theophylline that will bind the conjugate. Wicking continues moving the mouse anti-theophylline-theophylline complex and mouse anti-theophylline conjugate complex through zone 200 where the mouse anti-theophylline and all complexes containing mouse antibody are removed by binding to zone 200. Unbound conjugate moves onward through zone 202 and is bound to the anti-BSA that is non-diffusively immobilized in zone 202. In samples without theophylline present, the conjugate will be substantially all bound by mouse anti-theophylline (diffusively immobilized) in zone 198 and subsequently become bound to zone 200. Therefore, little or no gold will be free to move to zone 202 and produce a signal. In the case of very high concentrations of theophylline, the mouse anti-theophylline in zone 196 will be substantially all used in binding sample theophylline, and the conjugate will thus flow through zone 200 and become bound to zone 202, producing a maximal signal. Intermediate theophylline concentrations will produce color intensity on zone 202 that is directly proportional to the theophylline concentration in the sample. The instrument will make a comparison of the color intensity of zones 200 and 202, and based on a calibration, the instrument display gives a quantitative reading.

Figure 19:
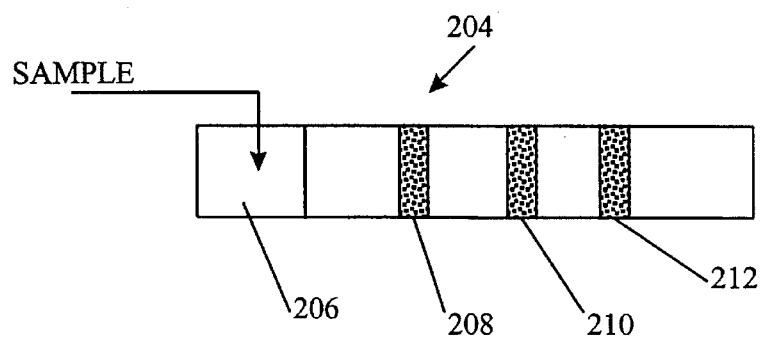
FIG. 19 shows a top surface view of a multiple immunoassay that measures THC (tetrahydrocannabinol) and morphine.

FIG. 19 shows a top surface view of a multiple immunoassay that measures THC (tetrahydrocannabinol) and morphine. In this embodiment, zone 206 of strip 204 contains diffusively bound two conjugates, the first conjugate of colloidal gold or enzyme to THC and BSA and the second conjugate of colloidal gold or enzyme to morphine and BSA. Zone 208 contains non-diffusively bound anti-THC. Zone 210 contains anti-morphine non-diffusively bound. Zone 212 contains anti-BSA non-diffusively bound. Two assays are shown here, however, the method can measure 1, 2, 3, 4, 5, 6 and more hapten or protein analytes simultaneously.

In this embodiment, the operation of this assay is identical to that described in FIG. 17. Each of the assays for multiple analytes operates independently since the antibodies are very specific. In the multiple assay configurations, the instrument will have multiple light sources (LED) and detectors to correspond to the number of reaction surfaces.

Figure 20:
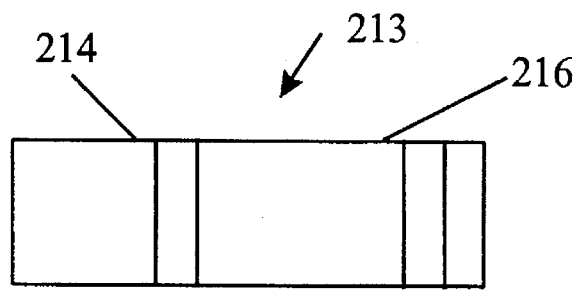
FIG. 20 shows a plain surface view of another embodiment of an immunoassay of this invention.
Figure 21:
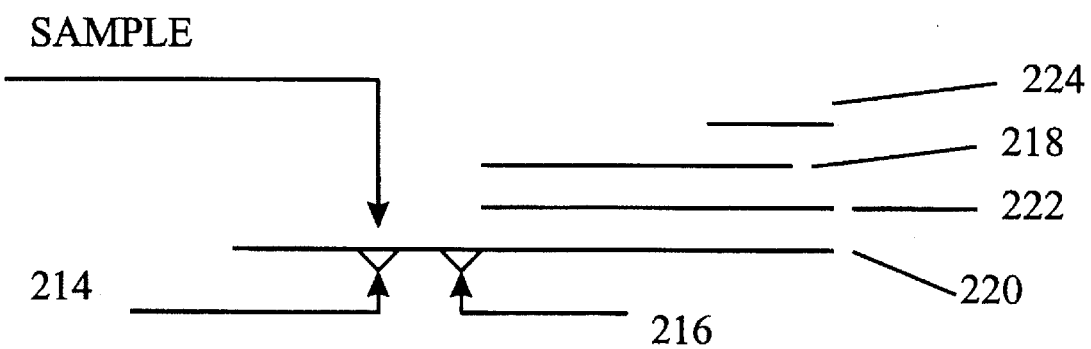
FIG. 21 shows an exploded longitudinal cross sectional view of the embodiment shown in FIG. 20.

FIG. 20 shows a plain surface view and FIG. 21 shows an exploded longitudinal cross section of another embodiment of an immunoassay of this invention. In this embodiment, zone 214 of strip 213 has diffusively bound anti-theophylline, and zone 216 has diffusively bound glucose-6-phosphate dehydrogenase (G6PDH) conjugated to theophylline. Zone 218 is a membrane that has diffusively immobilized the G6PDH substrates glucose-6-phosphate (G6P) and NAD. In addition, it is possible to add a tetrazolium salt, such as nitro blue tetrazolium, to the membrane of zone 218. Nitro blue tetrazolium is reduced to a blue colored diformazan which will likely result in an advantage over the yellow color produced when NAD is reduced to NADH. The assay strip configuration and materials are exactly as that described for the assay strip in FIGS. 7–10 with a sample transport matrix 220, membrane 222 and adhesive 224. Preferably, a sample filtration/blood separation device described in FIGS. 11 and 12 can added to pretreat the sample.

This assay chemistry is the chemistry of Syva EMIT™, adapted to be run on a dry reagent strip. The EMIT chemistry is a homogenous solution phase immunoassay system that is used for large clinical analyzers. For the purpose of the disposable instrument described here, the EMIT chemistry is formulated and configured to operate on a solid support. The EMIT chemistry patent has recently expired. The EMIT chemistry results in the measurement of an enzyme rate that is measured by the instrument. The enzyme rate as evidence by substrate turnover is directly proportional to the concentration of analyte in the sample. The EMIT technology has been used for more than 17 years in clinical laboratories to measure a wide variety of analytes of clinical interest including both small molecules and proteins such as drugs of abuse like THC, cocaine, morphine, amphetamine, methamphetamine, PCP, LSD, and barbiturate and therapeutic drugs such as theophylline, digoxin, phenobarbital, carbamazepine, phenatoin, and thyroid hormones like T3 and T4 and proteins like C-reactive protein. The example described below is a theophylline assay, however, as mentioned previously the EMIT technique can measure a wide variety of analytes.

In this embodiment, the sample is applied through the sample filtration device to zone 214 as shown in FIG. 20 and 21, where the theophylline in the sample mixes and is bound by the anti-theophylline diffusively bound in this zone. The sample and theophylline antibody and anti-theophylline-theophylline complex move via wicking action through zone 216 where the mixture encounters the G6PDH-theophylline conjugate. Unbound anti-theophylline binds to the conjugate and causes an inhibition of the G6PDH enzymatic activity. Wicking proceeds and the G6PDH conjugate-anti-theophylline complex moves into zone 218 where the substrates G6P and NAD are in excess and are turned over by the G6PDH at a rate that is dependent on the amount of anti-theophylline that is bound to the enzyme conjugate. In the case of a low theophylline concentration in the sample, only a small amount of anti-theophylline in zone 214 will be bound by sample, leaving the balance to bind with the enzyme conjugate in zone 216 and inhibit its activity. This will result in a relatively low turnover in zone 218. In the case of a very high concentration of theophylline in the sample, the antibody in zone 214 may be largely bound by the sample and not available to bind and inhibit the enzyme conjugate in zone 216. This situation will result in a maximal enzyme rate in zone 218. Intermediate concentrations of theophylline will produce enzyme inhibition that is inversely proportional to the theophylline concentration and final enzyme rates in zone 218 that are directly proportional to the theophylline concentration.

In the case of a solid phase EMIT as here described, the disposable instrument will measure enzyme rate by the increase in color in zone 218 rather than the endpoint color to the pad. This enzyme rate is converted to clinical units by the instrument based on a pre-programmed calibration.

The instrument of this invention is designed to be manufactured at a sufficiently low cost such that it is practical to dispose of the device after a single use. Current home or disposable on-site devices fall in the category of non-instrumented diagnostic devices. Examples of these devices include pregnancy (HCG) and ovulation (LH) tests and a variety of visual color comparison type dip sticks and migration height-type quantitative test such as the AccuMeter cholesterol and AccuLevel theophylline, phenobarbital and carbamazepine assays. Although these devices have proven to be accurate, color comparison is subjective and migration height assays are sometimes difficult to read and the test protocols require large sample volumes (about 50 μL for AccuMeter) with assay times of about 15 minutes. The most significant problem with non-instrumented assays is the required judgment or interpretation by the operator. This leads to errors. Also non-instrumented quantitative migration height assays are limited to the measurement of end point assays and cannot measure enzyme rate. This limits the potential menu of tests doable on these devices.

The present invention marks a significant advance in on-site diagnostics in that for the first time the idea of single use does not accompany non-instrumented. This invention marks a change in paradigm related to single use diagnostic self-tests. Previously anyone thinking of single use disposable diagnostic self-test would think only of non-instrumented devices.

Due to the rapid advances in solid state electronics in the area of cost reduction it is possible to make disposable diagnostic instruments.

Disposable instruments offer many advantages over traditional non-instrumented devices in that quantitative and qualitative results can be obtained faster (in about 3 minutes) and both endpoint and rate assays can be easily done. Therefore, the possible menu of tests is larger and the subjectivity and reading difficulties are eliminated since an LCD display provides a numerical result. In addition, since the devices use electronics, it is easily possible to add electronic compensation (like temperature compensation) and procedural controls that check for operator errors and reagent stability. The disposable instrumented device of this invention can be made to be more reliable than previously described non-instrumented self-tests.

This invention is further illustrated by the following specific, but non-limiting examples. In these examples, procedures which have been carried out in the laboratory are presented in the past tense, and procedures which are constructively reduced to practice herein are presented in the present tense. Unless otherwise specified, temperatures are in degrees Centigrade and percents are weight percents.

EXAMPLE 1

The assay chemistry device of the embodiment shown in FIGS. 9 and 10 is a duel assay strip measuring both total cholesterol and HDL cholesterol simultaneously. This device configuration is an improvement of the devices shown in the above-listed Kingston patents since it combines two of the Kingston strips described in the patents incorporated hereinabove in conjunction with the description of FIGS. 7 and 9, allowing two analytes to be measured simultaneously. One Kingston total cholesterol strip and one HDL cholesterol strip are placed end to end such that they have a common sample application area. The sample is applied in between each reagent strip and the sample moves in both directions allowing two analytes to be measured with a single sample application. The assay reagents, formulations, and strip configuration is otherwise the same as described in the above-referenced Kingston patents.

EXAMPLE 2

The devices of the embodiments shown in FIGS. 13–15 are qualitative antibody detection assays with an anti-HIV assay shown as an example. The assay strips shown in these embodiments can be configured such that the strip is composed of several sections in fluid communication by lamination to plastic support as shown in FIG. 12 (configuration 1) or the strip can be one continuous material (configuration 2). Configuration 1 and 2 will be considered in this example.

In Configuration 1, each zone of the assay strip is a separate piece of paper or membrane that has reagents immobilized to it in a separate process. The zones are then brought into fluid communication along the assay strip via lamination to a support. In this example the assay strip will be made of several sections of the chromatography paper WHATMAN 31ET that are in fluid communication. In the initial zone (zone 154 of FIG. 13, zone 162 of FIG. 14 and zone 170 of FIG. 15), the conjugate is diffusively bound. In the second zone (zone 156 of FIG. 13, zone 164 of FIG. 14 and zone 172 of FIG. 15), the protein reagents (HIV antigen, viral lysate, anti-P24 monoclonal, anti-human antibody, anti-fluorescein, or BSA (bovine serum albumin)) are non-diffusively bound using covalent immobilization. In FIGS. 13–15, each of the non-diffusively bound proteins is covalently bound to the cellulose support using the two step process described below.

Non-diffusive immobilization:

STEP 1: Activation of the cellulose support is accomplished by incubating a 20×25 cm sheet of 31ET chromatography paper in a standard lasagna dish (baking dish 23×28 cm) for 2 hours at room temperature in 500 mL of 0.2M 1,1'-Carbonyldiimidazole (CDL, Aldrich 11,553-3) in methylene chloride at room temperature. Following this incubation, the activated paper is washed extensively in several (4–8) 250 mL volumes of methylene chloride and dried under nitrogen. This procedure results in activated 31ET to which proteins or small molecules with primary amine functional groups can be covalently immobilized (non-diffusive binding).

STEP 2: Non-diffusive-immobilization of the protein to the activated 31ET paper is accomplished by incubating the activated 31ET in 150 mL of a 1.0 to 2.0 mg/mL solution of the desired protein in 0.1M sodium phosphate pH 7 at room temperature for two hours. The paper is then washed by incubation for 20 minutes in 500 mL of 0.1M sodium phosphate pH 7. The washing step is repeated 4 times, then the paper is soaked in 150 mL of 0.5% polyvinyl alcohol (PVA, Aldrich 18,965-0) for 10 minutes, gently blotted and dried in a convection oven at 45° C. for 10 to 30 minutes or until dry.

Non-diffusive immobilization of the conjugate is accomplished by mixing the conjugate from 0.0001 to 0.1 mg/mL (depending on the assay) with 0.1% surfactant and/or 0.1% glycerol and/or 1% polyethylene glycol in 0.1M sodium phosphate at pH 7 and placing 10 μl of this in zone (154, 162, 170) and drying for 10 to 30 minutes at 45° C. or until dry. Zone (154, 162, 170) is inactivated 31ET and the conjugate is dried but is free to move once reconstituted by the sample.

In Configuration 2, the assay reagents are non-diffusively immobilized along a continuous strip by using a soak and dry method, or by immobilizing the protein to latex microparticles of about 5–20 μm and drawing these conjugated microparticles into the membrane matrix using vacuum pressure. This is an alternate approach that can be used for the non-diffusive immobilization in the second, third and fourth zones of FIGS. 13–15.

The spot and dry immobilization method is accomplished by applying 10 μL of a mixture containing 0.5% dextran (MW=2,000,000) and the desired protein at 0.1 to 10 mg/mL in 0.1M sodium phosphate pH 7 to the desired strip location and drying rapidly using a blow dryer. The mixture can also be applied by spray immobilization and rapid drying.

The microparticle method is accomplished by first covalently immobilizing the desired protein to Bangs microspheres with carboxyl functional groups as follows: To a suspension of 10 μm microspheres-COOH (Bangs stock no. P0100000CN) add 1.1 molar equivalent (relative to the COOH groups on the bead surface) of 1-ethyl-3-(dimethylaminopropyl)carbodiimide (EDAC, Sigma E 0388) and 1.1 molar equivalent of N-Hydroxysuccinimide (NHS, Pierce 24500) in 0.1M sodium phosphate pH 7 at room temperature with stirring for 30 minutes. Add this mixture to a stirring solution of the desired protein in 0.1M sodium phosphate pH 7 (the protein is at a 10 fold molar excess over the COOH functional groups on the bead surface). Allow to react for 2 hours at room temperature, then purify via gel filtration and dialysis or membrane filtration with washing. The microparticles now have the desired protein covalently immobilized.

The protein-particle suspension is then mixed and 5 μL is picked up using a pipette. The membrane or paper assay strip is placed on a sintered glass filtration platform with vacuum and the bead-protein suspension is applied from the pipette across the assay strip in the correct location. The vacuum pressure draws the conjugated beads into the matrix of the membrane or paper where they are mechanically non-diffusively immobilized.

EXAMPLE 3

The device of the embodiment shown in FIG. 16 is a qualitative pregnancy (HCG) assay. In zone 180, a conjugate of polyclonal anti-αHCG and latex bead is diffusively immobilized to untreated 31ET as described in Example 2 at a concentration of 0.001 mg/mL. In zone 182, mouse monoclonal anti-βHCG is non-diffusively immobilized at 1 mg/mL and in zone 184, polyclonal anti-HCG at 2 mg/mL is non-diffusively immobilized, according to the procedures described in Steps 1 and 2 of Example 2.

Alternately, the spot and dry method can be used with the diffusive immobilization of the conjugate to zone 180 accomplished as described above. The non-diffusive immobilization in zones 182 and 184 of FIG. 16 is done by spotting a 2 mg/mL solution of mouse anti-βHCG (zone 182) or anti-goat antibody (zone 184) with 0.5% dextran (MW=2,000,000) in sodium phosphate at pH 7 in the appropriate strip area. The protein spot is then dried rapidly using a blow dryer. In this example, a 12μ nitrocellulose membrane from Schleicher and Schuell is used as the assay matrix.

Alternately, the microparticle method can be used for the non-diffusive immobilization of the antibodies in zones 182 and 184. Microparticles with carboxyl functional groups are incubated with 1.1 molar equivalents of EDAC and NHS for 30 minutes. These activated microparticles are then added to a stirring solution of 2 mg/mL of either anti-βHCG or anti-goat antibody for 2 hours at room temperature (20°–25° C.). Following purification using membrane filtration and washing beads are immobilized using the vacuum method to the desired strip location. This procedure is described in Example 2.

EXAMPLE 4

The device in FIGS. 17–19 shows a quantitative assay (when used with the single use instrument) for a small molecule such as theophylline or drugs of abuse.

In FIG. 17, the conjugate of the theophylline to colloidal gold (or enzyme) and BSA is diffusively bound according to example 2 at 0.001 mg/mU Zone 190 has anti-theophylline immobilized non-diffusively following the 2 step procedure of Example 2 at 1 mg/mL. Zone 192 contains BSA non-diffusively immobilized at 2 mg/mL according to Example 2.

FIG. 18 has mouse anti-theophylline diffusively immobilized at 10 mg/mL in zone 196. Zone 198 has diffusively immobilized at 10 mg/mL (a conjugate of theophylline) to colloidal gold (or enzyme) and BSA. Zone 200 has anti-mouse antibody non-diffusively immobilized at 2 mg/mL, and zone 202 has BSA non-diffusively immobilized at 2 mg/mL according to the two step procedure of Example 2.

FIG. 19 is a multiple assay for drugs of abuse measuring both THC and morphine. Zone 206 has two conjugates including a conjugate of THC to colloidal gold (or enzyme) and BSA, and a conjugate of morphine to colloidal gold (or enzyme) and BSA. Both conjugates are immobilized diffusively at 0.001 mg/mL according to Example 2. Zones 208, 210, and 212 have non-diffusively bound proteins (anti-THC, anti-morphine, and anti-BSA, respectively). Each of the proteins is immobilized at 2 mg/mL.

Alternately, the dip and dry or microparticle method of non-diffusive immobilization can be used as described in Examples 2 and 3. In this case, the assay matrix will be Schleicher and Schuell 12μ nitrocellulose.

EXAMPLE 5

The device of embodiment shown in FIGS. 20 and 21 is a solid phase EMIT assay. EMIT technology was first introduced by Syva Company in 1972 as a homogeneous solution phase assay. This example demonstrates an EMIT assay on a solid support.

Anti-theophylline antibody is diffusively immobilized by applying 10 μL of a solution containing 0.5% dextran (MW=2,000,000) and 5 mg/mL of anti-theophylline in 0.1M sodium phosphate pH 7 to the zone 214 position of the sample transport matrix and quickly drying the area with a heated blow dryer. The conjugate of G6PDH (Glucose-6-phosphate dehydrogenase, EC 1.1.1.49) and theophylline is diffusively immobilized at 5 mg/mL using a similar procedure. The reaction membrane (zone 218) contains the G6PDH substrates glucose-6-phosphate (G6P) and nicotinamide adenine dinucleotide (NAD) and the tetrazolium salt. The membrane of zone 218 is dipped in 50 mM G6P (glucose-6-phosphate, Sigma G7879), 50 mM NAD (Sigma N1636), and 0.5 mg/mL nitro blue tetrazolium (Sigma N6876) with 2 mg/mL BSA in sodium phosphate pH 7 and dried in a convection oven at 45° C. for 15 minutes.

Although preferred embodiments of the subject invention have been described in some detail, it is understood that obvious variations can be made without departing from the spirit and the scope of the invention as defined by the appended claims.

EXAMPLE 6

Assay Strip Preparation:

The device of the embodiment shown in FIG. 16 is a qualitative pregnancy (HCG) assay. In zone 180 a conjugate of polyclonal anti-αHCG and colloidal gold is diffusively immobilized to untreated 12 μm nitrocellulose as described in example 2 at a concentration of 0.001 mg/mL. In zone 182 mouse monoclonal anti-βHCG is non-diffusively immobilized at 1 mg/mL and in zone 184 polyclonal anti-HCG is non-diffusively immobilized at 2 mg/mL to the 12 µm nitrocellulose membrane.

The antibodies are non-diffusively immobilized to zones 182 and 184 using the following procedure:

1) The antibody at the above mentioned concentration is mixed with BSA bulking protein at 2 mg/mL and 0.25% dextran T-2,000,000 (as a method of increasing viscosity) in a pressurized vessel fitted with a spray nozzle. The spray nozzle is set up to produce a uniform spray stream with a 1 mm width.

2) The nitrocellulose membrane is positioned on a moving nylon screen such that it passes under the spray nozzle and immediately into a heated drying chamber.

3) The spray nozzle applies a precise amount of antibody solution to the moving membrane such that a 1 mm zone of antibody is applied across the membrane.

4) The antibody on the membrane is immediately dried as it is moved through the drying chamber which is set at 70° C. The membrane moves through the drying chamber for 15 minutes or until dry.

The antibody is now non-diffusively immobilized to the nitrocellulose membrane via non-specific adsorption.

Instrument signal detection:

In this embodiment a sample that contains HCG will produce a concentration of the colloidal gold in zone 182. The presence of this signal can be detected using optical methods as described in example 3 or the electrical conductivity of the gold can be used as a detection method. In the embodiment of this example the excellent conductivity of the gold is used to detect the presence of the signal in zones 182 and 184. Electrodes are placed on both sides of zone 182 such that in the presence of gold in this zone an electrical path will be created that completes a circuit resulting in a low resistance. In the absence of gold binding to zone 182 no electrical path will exist resulting in a high resistance. The binding of gold to zones 182 or 184 can be detected by conductivity, resistance or the like. This eliminates the need for the sophisticated optics and reduces the complexity of the processor. This is a cost reducing method that can be used for the HCG assay of this example as well as the AIDS assay of example 2.

The Invention claimed is:

1. A single-use assay device comprising:

a unitary housing having an exterior surface and sealing an interior area;

sample receptor means for receiving a sample containing an analyte selected for determining its presence, the sample receptor means being located on the exterior surface of the housing;

sample treatment means for reacting the sample with a self-contained reagent to yield a physically detectable change which correlates with the amount of selected analyte in the sample, the sample treatment means being sealed within the housing and in fluid communication with the sample receptor means;

detector means for responding to the physically detectable change and producing an electrical signal which correlates to the amount of the selected analyte in the sample, the detector means being sealed within the housing and in electrical or optical communication with the sample treatment means;

processing means for storing assay calibration information, the assay calibration information being uniquely characteristic to the specific self-contained reagent and physically detectable change of the sample treatment means and to the specific detector means of the individual assay device, the processing means further calibrating the sample treatment means and the detector means using the stored assay calibration information, and the processing means further converting the electrical signal to a digital output, the processing means being sealed within the housing and connected to the detector means; and display means for visually displaying the digital output external to the housing, the display means being connected to the processing means.

2. The assay device of claim 1 wherein the processing means further calibrates the detector means to a reference standard using the stored assay calibration information.

3. The assay device of claim 1 wherein the processing means further receives the ambient temperature of the assay device from a sensor within the housing and adjusts the assay results using the stored assay calibration information.

4. The assay device of claim 1 wherein the processing means further compares the stored assay calibration information with the electrical signal to determine the accuracy of the assay, the stored assay calibration information including a pre-determined range for the electrical signal.

5. The assay device of claim 1 wherein the processing means further compares the stored assay calibration information with the digital output to determine the accuracy of the assay, the stored assay calibration information including a pre-determined range for the digital output.

6. The assay device of claim 1 wherein the processing means further includes a timer which measures shelf-life of the device and, after a pre-determined period, sends a warning message as the digital output signal to the display means or disables the device.

7. The assay device of claim 1 wherein the sample receptor means includes a sensor for determining the presence of the sample and sending a signal to the processing means, the processing means further clocks the signal and compares the clocked signal to the stored assay calibration information to determine the accuracy of the assay, the stored assay calibration information including a pre-determined range for the clocked signal.

8. A single-use assay device comprising:

a unitary housing having an exterior surface and sealing an interior area;

sample receptor means for receiving a sample containing an analyte selected for determining its presence, the sample receptor means being located on the exterior surface of the housing, the sample receptor means including a reference-on sensor for determining the presence of the sample and sending a reference-on signal to a processing means;

sample treatment means for reacting the sample with a self-contained reagent to yield a physically detectable change which correlates with the amount of selected analyte in the sample, the sample treatment means being sealed within the housing and in fluid communication with the sample receptor means, the sample treatment means including a read-on sensor for determining the presence of the sample and sending a read-on signal to the processing means;

detector means for responding to the physically detectable change and producing an electrical signal which correlates to the amount of the selected analyte in the sample, the detector means being sealed within the housing and in electrical or optical communication with the sample treatment means;

processing means storing assay calibration information, the assay calibration information being uniquely characteristic to the specific self-contained reagent and physically detectable change of the sample treatment means and to the specific detector means of the individual assay device, the processing means further calibrating the sample treatment means and the detector means using the stored assay calibration information, and the processing means further converting the electrical signal to a digital output, the processing means being sealed within the housing and connected to the detector means, the processing means further monitoring the reference-on and read-on signals and comparing the signals to the stored assay calibration information to determine that the reaction has occurred within a specified time and a specified reaction rate to check the accuracy of the assay, the stored assay calibration information including a pre-determined range for the signals; and display means for visually displaying the digital output external to the housing, the display means being connected to the processing means.

9. A single-use assay device comprising:

a unitary housing having an exterior surface and sealing an interior area;

sample receptor means for receiving a sample containing an analyte selected for determining its presence, the sample receptor means being located on the exterior surface of the housing;

sample treatment means for chemically reacting the sample with a self-contained reagent in a reaction zone to produce a reaction product mixture, the sample treatment means further transporting at least a portion of the reaction product mixture to a detection zone, the sample treatment means being sealed within the housing and in fluid communication with the sample receptor means;

detector means for responding to a physically detectable change in the detection zone which correlates with the amount of selected analyte in the sample and producing an electrical signal which correlates to the amount of the selected analyte in the sample, the detector means being sealed within the housing and in electrical or optical communication with the sample treatment means;

processing means storing assay calibration information, the assay calibration information being uniquely characteristic to the specific self-contained reagent and physically detectable change of the sample treatment means and to the specific detector means of the individual assay device, the processing means further calibrating the sample treatment means and the detector means using the stored assay calibration information, and the processing means further converting the electrical signal to a digital output, the processing means being sealed within the housing and connected to the detector means; and display means for visually displaying the digital output external to the housing, the display means being connected to the processing means.

10. The single-use assay device of claim 9 wherein the portion of the reaction mixture which is transported to the detection zone includes a reaction product with a physically detectable label which correlates with the amount of the selected analyte in the sample.

11. The single-use assay device of claim 9 wherein the portion of the reaction mixture which is transported to the detection zone includes the sample with undesired substances removed, the sample reacting with a second self-contained reagent in the detection zone to produce a reaction product with a physically detectable label which correlates with the amount of selected analyte in the sample.

12. The single-use assay device of claim 9 wherein the device further includes a power source in electrical connection with the detector means and the processing means, the power source sealed within the housing.

13. The single-use assay device of claim 9 wherein the device further includes a power source in electrical connection with the detector means and the processing means, the power source is a solar cell mounted on the exterior of the housing.

14. The single-use assay device of claim 9 wherein the physically detectable label provides a change in reflectance or transmission of the detection zone, and the detector includes a light source positioned to direct light on the detection zone and a light detector positioned to receive light reflected or transmitted by the detection zone to yield a respective reflectance or transmission output signal.

15. The single-use assay device of claim 4 wherein said light source consists of a single light emitting diode and light piping communicating the light emitting diode with the detection zone.

16. A single-use device for performing a plurality of assays, the multi-assay device comprising:

a unitary housing having an exterior surface and sealing an interior area;

sample receptor means for receiving a sample containing at least one of a plurality of analytes selected for determining its presence, the sample receptor means being located on the exterior surface of the housing;

sample treatment means for chemically reacting the sample with a plurality of self-contained reagents corresponding to the plurality of assays, each self-contained reagent chemically reacting with the sample in a corresponding reaction zone located on a transport matrix to produce a reaction product mixture corresponding to each self-contained reagent, the sample treatment means further transporting at least a portion of each reaction product mixture to a corresponding detection zone located on the transport matrix, the sample treatment means being sealed within the housing and in fluid communication with the sample receptor means;

detector means for responding to a physically detectable change in each detection zone which correlates with the amount of selected analyte in the sample and producing a corresponding electrical signal which correlates to the amount of the selected analyte in the sample, the detector means being sealed within the housing and in electrical or optical communication with the sample treatment means;

processing means storing assay calibration information, the assay calibration information being uniquely characteristic to each specific self-contained reagent and each specific physically detectable change of the sample treatment means and to the specific detector means of the individual multi-assay device, the processing means further calibrating the sample treatment means and the detector means using the stored assay calibration information, and the processing means further connected to the detector means for converting each electrical signal to a corresponding digital output, the processing means being sealed within the housing;

display means for visually displaying each digital output external to the housing, the display means being connected to the processing means.

17. The multi-assay device of claim 16 wherein the portion of each reaction mixture which is transported to the corresponding detection zone includes a reaction product with a physically detectable label which correlates with the amount of the corresponding selected analyte in the sample.

18. The multi-assay device of claim 16 wherein the portion of each reaction mixture which is transported to the corresponding detection zone includes the sample with undesired substances removed, the sample chemically reacting with a second plurality of self-contained reagents in each corresponding detection zone to produce a reaction product with a physically detectable label which correlates with the amount of the corresponding selected analyte in the sample.

19. The multi-assay device of claim 16 wherein the sample contains more than one analyte selected for determining its presence, each self-contained reagent corresponds to one of the selected analytes.

20. The multi-assay device of claim 16 wherein each physically detectable change provides a change in reflectance or transmission of each detection zone, and the detector means includes a light source positioned to direct light on each detection zone and a light detector positioned to receive light reflected or transmitted by each detection zone to yield a respective reflectance or transmission output signal corresponding to each physically detectable change.

21. The multi-assay device of claim 16 wherein the light source includes a single light emitting diode and light piping connecting the light emitting diode to each detection zone.

22. A single-use device for performing a plurality of assays, the multi-assay device comprising:

a unitary housing having an exterior surface and sealing an interior area;

sample receptor means for receiving a sample containing at least one of a plurality of analytes selected for determining its presence, the sample receptor means being located on the exterior surface of the housing;

sample treatment means for reacting the sample with a plurality of self-contained reagents corresponding to the plurality of assays, each self-contained reagent reacting with the sample in a corresponding reaction zone located on a transport matrix to produce a reaction product mixture corresponding to each self-contained reagent, the sample treatment means further transporting a portion of each reaction product mixture to a corresponding detection zone located on the transport matrix, the sample treatment means being sealed within the housing and in fluid communication with the sample receptor means;

detector means for responding to a physically detectable change in each detection zone which correlates with the amount of the corresponding selected analyte in the sample and producing a corresponding electrical signal which correlates to the amount of the corresponding selected analyte in the sample, the detector means being sealed within the housing and in electrical or optical communication with the sample treatment means;

processing means storing assay calibration information, the assay calibration information being uniquely characteristic to each specific self-contained reagent and to each specific physically detectable change of the sample treatment means and to the specific detector means of the individual assay device, the processing means further calibrating the sample treatment means and the detector means using the stored assay calibration information, and the processing means further converting each electrical signal to a corresponding digital output, the processing means being sealed within the housing and connected to the detector means;

a power source in electrical connection with the detector means and the processing means, the power source sealed within the housing; and display means for visually displaying each digital output external to the housing, the display means being connected to the processing means.

23. The multi-assay device of claim 22 wherein the portion of each reaction mixture which is transported to the corresponding detection zone includes a reaction product with a physically detectable label which correlates with the amount of the corresponding selected analyte in the sample.

24. The multi-assay device of claim 22 wherein the portion of each reaction mixture which is transported to the corresponding detection zone includes the sample with undesired substances removed, the sample chemically reacting with a second plurality of self-contained reagents in each corresponding detection zone to produce a reaction product with a physically detectable label which correlates with the amount of the corresponding selected analyte in the sample.

25. A method of determining the presence of one or more selected analytes in a sample, the method comprising the steps of:

introducing the sample to the sample receptor means of the assay device of claim 9, transporting the sample to the reaction zone within the sealed housing;

chemically reacting the sample with the self-contained reagent to produce a reaction product mixture;

transporting at least a portion of the reaction product mixture to the detection zone;

producing a physically detectable change in the detection zone and an electrical signal which correlates with the amount of the corresponding selected analyte in the sample;

calibrating the physically detectable change using said stored assay calibration information uniquely characteristic to the specific self-contained reagent and physically detectable change of the individual sealed housing;

converting the electrical signal to a digital output;

displaying the digital output; and disposing of the sealed housing after one introduction of the sample.

26. The method of claim 25 wherein, prior to the processing step, the method further includes the step of:

chemically reacting the portion of the reaction mixture transported to the detection zone with a second self-contained reagent to produce a reaction product with a physically detectable label which correlates with the amount of selected analyte in the sample.

27. The method of claim 25 wherein the method further includes the step of calibrating the measuring step to a reference standard using the stored information.

28. The method of claim 25 wherein the method further includes the steps of receiving the ambient temperature of the assay device from a sensor within the housing and adjusting the assay results using the stored information.

29. The method of claim 25 wherein the method further includes the step of comparing the stored information with the electrical signal to determine the accuracy of the assay, the stored information including a pre-determined range for the electrical signal.

30. The method of claim 25 wherein the method further includes the step of comparing the stored information with the digital output to determine the accuracy of the assay, the stored information including a pre-determined range for the digital output.

31. The method of claim 25 wherein the method further includes the steps of timing the presence of the sample and comparing the timed presence of the sample to the stored information to determine the accuracy of the assay, the stored information including a pre-determined range for the timed presence of the sample.

* * * * *